United States Patent
De Poly et al.

(10) Patent No.: US 11,922,623 B2
(45) Date of Patent: Mar. 5, 2024

(54) CELLULAR DIAGNOSTIC AND ANALYSIS METHODS

(71) Applicant: Aquyre Biosciences, Inc., Boston, MA (US)

(72) Inventors: Bertrand Le Conte Chrestien De Poly, Boston, MA (US); Emilie Benoit A La Guillaume, Boston, MA (US); Zoya I. Volynskaya, Boston, MA (US)

(73) Assignee: Aquyre Biosciences, Inc., Boston, MA (US)

( * ) Notice: Subject to any disclaimer, the term of this patent is extended or adjusted under 35 U.S.C. 154(b) by 315 days.

(21) Appl. No.: 17/374,830

(22) Filed: Jul. 13, 2021

(65) Prior Publication Data
US 2022/0012879 A1 Jan. 13, 2022

Related U.S. Application Data

(60) Provisional application No. 63/051,117, filed on Jul. 13, 2020.

(51) Int. Cl.
*A61B 17/34* (2006.01)
*G06T 7/00* (2017.01)

(52) U.S. Cl.
CPC ........ *G06T 7/0012* (2013.01); *A61B 17/3403* (2013.01); *G06T 2207/20084* (2013.01); *G06T 2207/20182* (2013.01); *G06T 2207/30024* (2013.01)

(58) Field of Classification Search
None
See application file for complete search history.

(56) References Cited

U.S. PATENT DOCUMENTS

| | | | |
|---|---|---|---|
| 5,240,606 A | 8/1993 | Lapidus et al. | |
| 6,940,602 B2 | 9/2005 | Dubois et al. | |
| 7,483,554 B2 | 1/2009 | Kotsianti et al. | |
| 9,185,357 B2 | 11/2015 | Boccara et al. | |

(Continued)

FOREIGN PATENT DOCUMENTS

| | | |
|---|---|---|
| FR | 2962531 B1 | 1/2014 |
| JP | 6943459 B2 | 9/2021 |

(Continued)

OTHER PUBLICATIONS

Apelian et al.; Dynamic full field optical coherence tomography: subcellular metabolic contrast revealed in tissues by interferometric signals temporal analysis; Biomedical Optics Express; 7(4); pp. 1511-1524; 14 pages; (Author Manuscript); Apr. 2016.

(Continued)

*Primary Examiner* — Idowu O Osifade
(74) *Attorney, Agent, or Firm* — Shay Glenn LLP

(57) ABSTRACT

Detection of pathological abnormalities in tissue samples and/or pluralities of cells is a highly specialized and time-consuming effort, usually performed by a select group of clinicians and technical personnel. Described herein are methods for more automatable, consistent and comprehensive cell sample analysis to deliver a rapid, reliable and detailed classification, e.g., diagnosis, of the status of cells present in a sample, particularly, but not limited to cancer diagnosis.

19 Claims, 19 Drawing Sheets
(14 of 19 Drawing Sheet(s) Filed in Color)

(56) References Cited

U.S. PATENT DOCUMENTS

| | | | |
|---|---|---|---|
| 9,255,785 | B2 | 2/2016 | Boccara et al. |
| 9,541,477 | B2 | 1/2017 | Saqi et al. |
| 10,229,488 | B2 | 3/2019 | Yu et al. |
| 10,533,932 | B2 | 1/2020 | Guldberg et al. |
| 10,627,613 | B2 | 4/2020 | Boccara et al. |
| 10,712,245 | B2 | 7/2020 | Thomsen et al. |
| 10,890,513 | B2 | 1/2021 | Mukaisho et al. |
| 10,962,454 | B2 | 3/2021 | Musat |
| 11,092,424 | B2 * | 8/2021 | Lipson .................. G02F 1/3528 |
| 2009/0221920 | A1 | 9/2009 | Boppart et al. |
| 2013/0229663 | A1 | 9/2013 | Liu et al. |
| 2014/0080171 | A1 | 3/2014 | Gimzewski et al. |
| 2016/0150961 | A1 | 6/2016 | Milner |
| 2017/0248503 | A1 | 8/2017 | Kshirsagar et al. |
| 2020/0233198 | A1 | 7/2020 | Boccara et al. |
| 2021/0190643 | A1 | 6/2021 | You et al. |
| 2021/0244374 | A1 * | 8/2021 | Zhao ..................... A61B 6/5282 |

FOREIGN PATENT DOCUMENTS

| | | |
|---|---|---|
| KR | 100632342 B1 | 10/2006 |
| WO | WO2017/174743 A1 | 10/2017 |

OTHER PUBLICATIONS

Apelian et al.; Extracting relevant information for cancer diagnosis from dynamic full field OCT through image processing and learning; (Conference Presentation); Optical Coherence Tomography and Coherence Domain Optical Methods in Biomedcine XXI; International Spciety for Optics and Photonics; vol. 10053; p. 100531H; 7 pages; Feb. 2017.

Apelian et al.; Pancreatic cancer study based on full field OCT and dynamic full field OCT; (Conference Presentation); InAdvanced Biomedical and Clinical Diagnostic and Surgical Guidance Systems XV; International Society for Optics and Photonics; vol. 10054; p. 100540N; 16 pages; Apr. 2017.

Mandache et al.; Blind sorce separation in dynamic cell imaging using non-negative matrix factorization applied to breast cancer biopsies; 18th International Symposium on Biomedical Imaging (ISBI); pp. 1605-1608; Apr. 2021.

Mandache et al.; Leveraging global diagnosis for tumor localization in dynamic cell imaging of breast cancer tissue towards fast biopsying; IEEE 1th International Symposium on Biomedical Imaging (ISBI); pp. 320-323; (Author Manuscript); Apr. 2021.

* cited by examiner

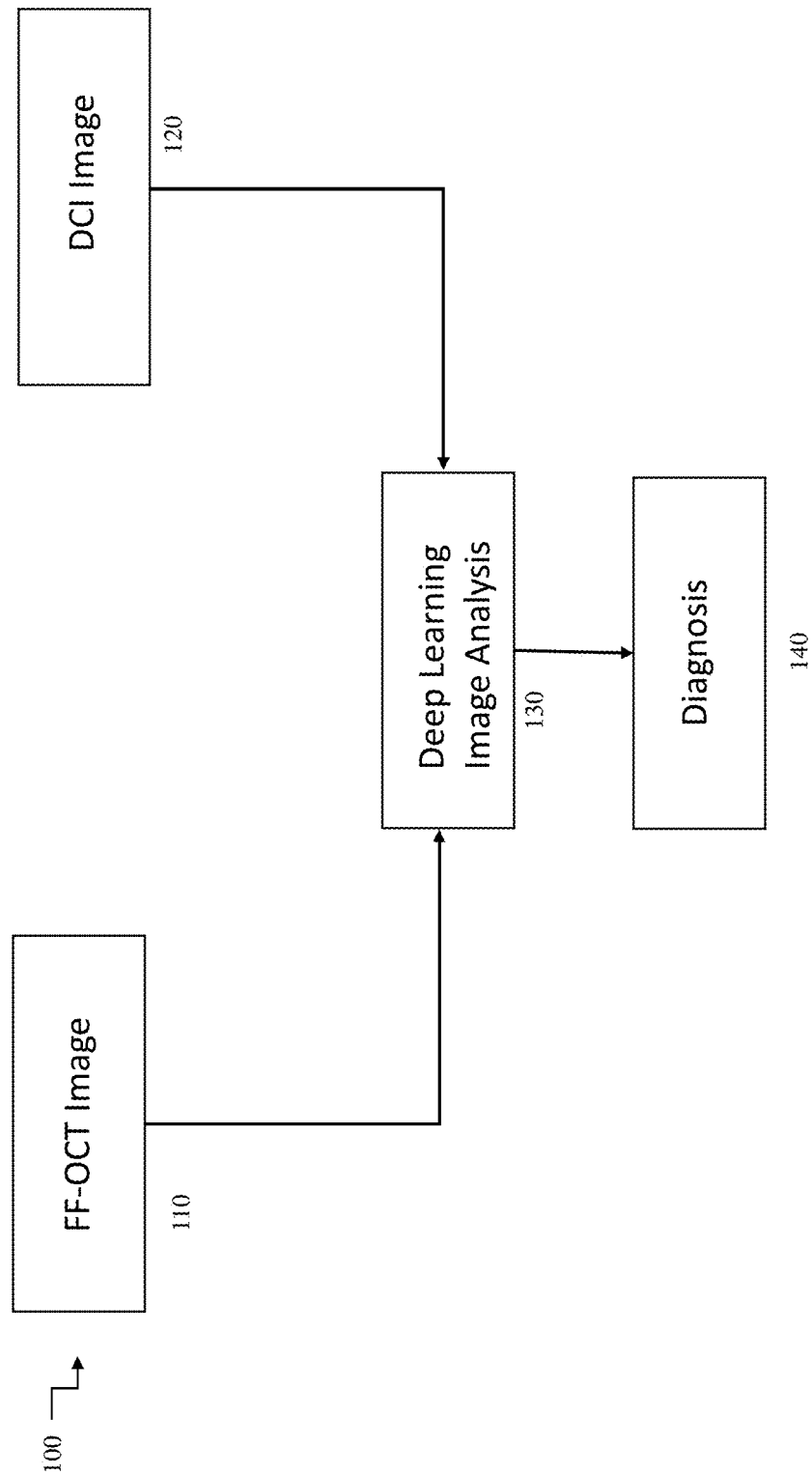

CELLULAR DIAGNOSTIC AND ANALYSIS METHODS

CROSS REFERENCE TO RELATED APPLICATIONS

This application claims the benefit of priority of U.S. Provisional Application No. 63/051,117, filed Jul. 13, 2020, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods describe herein relate to detection and determination of the status of cells and their environment within a sample, particularly within the field of cancer diagnostics, using optical imaging methods to enhance sample collection, increase diagnosis accuracy and speed, and lower costs.

BACKGROUND

Detection of pathological abnormalities in tissue samples and/or pluralities of cells is a highly specialized and time-consuming effort, usually performed by a select group of clinicians and technical personnel. The costs due to personnel resources and due to delay in time between biopsy procurement and delivery of diagnosis to a patient and/or the physician responsible for determining next steps are high. There are additional costs when delivery of timely treatment to the patient is delayed as well. Further, the analysis performed can be irreproducible from one practitioner to another, relying to some extent on subjective observation and interpretation. Therefore, it would be highly useful to provide a more automatable, consistent and comprehensive method to analyze samples derived from a patient to deliver a rapid, reliable and detailed classification, e.g., diagnosis, of the status of cells present in the patient sample, particularly, but not limited to cancer diagnosis.

SUMMARY OF THE DISCLOSURE

Methods are described herein which provide a more automatable, consistent and comprehensive method to analyze samples derived from a patient to deliver a rapid, reliable and detailed classification, e.g., diagnosis, of the status of cells present in the patient sample, particularly, but not limited to cancer diagnosis. Methods of analysis combining data available from both spatially-dependent interferometric images and time-dependent interferometric images can lead to a great increase in accuracy of assignment of status of the cells under examination.

The methods described herein have the potential to change the way cancer is diagnosed and treated as well. This is the direct or indirect goal of Rapid On Site Evaluation (ROSE), frozen sections, Confocal Laser Endomicroscopy (CLE), ultrasound, and other imaging modalities, but none of these diagnostic approaches has the potential to identify key indicators of tumor presence, tumor type, likely tumor response to a given therapy, or likelihood of recurrence after surgery in real time, non-destructively. The data available from the images obtained in the methods described herein, which include real time data, detailed images, dynamic cellular information, and viable tissue for further analysis all point to a wealth of valuable clinical, biologic, and structural data not available by any other single method. It can also be employed in parallel with other modalities like CLE, ultrasound, and traditional tissue processing methods because of its non-destructive nature. And finally, its non-destructive character opens up a wealth of potential downstream uses that cannot be achieved with current methods like frozen sections, which by their nature alter the tissue sample and potentially add sampling bias by not providing complete information about the surface of the sample.

Accordingly, in a first aspect a method is provided for determining the status of a plurality of cells, including: obtaining a time-dependent interferometric image and a spatially-dependent interferometric image of a plurality of cells suspected to include a cancerous cell; submitting the time-dependent interferometric image and the spatially-dependent interferometric image to a multi-layered algorithm analysis, thereby combining data associated at each pixel of the respective image of the plurality of cells; and automatically assigning a status to at least one cell of the plurality of cells, where the status is selected from a normal cell status or a cancerous cell status.

In some variations, the method may further include training the multi-layered algorithm analysis by analyzing a portion of data from the time-dependent interferometric image and/or a portion of data from the spatially-dependent interferometric image. In some variations, a time-dependent interferometric image and a spatially-dependent interferometric image may be spatially registered.

In some variations, the method may further include submitting an image of the plurality of cells, where the plurality of cells further include a detectable label, to the multi-layered algorithm analysis. In some variations, the method may further include: differentiating structural features of the plurality of cells; and reducing interference in the time-dependent interferometric image of the plurality of cells.

In some variations, the multi-layer algorithm analysis may include a pre-trained convolutional neural network.

In some variations, the method may further include automatically assigning a status to a sub-set of the plurality of cells, whereby a region in which the sub-set of the plurality of cells are disposed is annotated as normal or cancerous. In some variations, a sub-set of the structural features from the spatially-dependent interferometric images may be submitted to an artificial intelligence analysis, e.g., a deep learning algorithm, to thereby assign the status of the region in which the sub-set of the plurality of cells is disposed.

In another aspect, a method is provided for performing a biopsy on a subject in need thereof, including: imaging a region of tissue to identify a region of interest; inserting a biopsy needle into the region of interest; excising a first tissue sample from the region of interest; obtaining a set of time-dependent interferometric images and a spatially-dependent interferometric image of the first tissue sample; and determining a number of cells of interest present within the first tissue sample. In some variations, imaging the region of tissue, inserting the biopsy needle, excusing the first tissue sample, obtaining the set of time-dependent interferometric images and the spatially-dependent interferometric image, and determining the number of cells of interest present may be performed within a biopsy procedural theater.

In some variations, obtaining the set of time-dependent interferometric images and spatially-dependent image may further include processing the images to obtain images of sub-cellular metabolic activity of a plurality of cells within the first tissue sample.

In some variations, the method may further include assigning a status to one or more cells of the plurality of cells, where the one or more cells having the assigned status is a cell of interest. In some variations, the assigned status may be a diseased cell status. In some variations, the diseased cell status may be a cancerous cell status.

In some variations, determining a number of cells of interest includes submitting the images of sub-cellular metabolic activity to processing by a multi-layer algorithm, thereby assigning the status to the one or more cells. In some variations, assigning the status to the one or more cells may include comparing a level of metabolic activity observed in the one or more cells to a preselected threshold.

In some variations, the method may further include obtaining a second tissue sample from the region of interest, when the number of cells of interest in the first tissue sample is insufficient for analysis.

In some variations, imaging the region of tissue may include contrast optical imaging, label-free optical imaging, radiotopic imaging, ultrasound imaging or magnetic imaging. In some variations, inserting a biopsy needle may include guided insertion.

In another aspect, a method is provided for determining the status of a plurality of cells, including: obtaining images of sub-cellular metabolic activity of a plurality of cells suspected to include a cancerous cell, where the images include time-dependent interferometric images; automatically assigning a status to at least a sub-set of the plurality of cells, where the status is selected from a normal cell status or a cancerous cell status; and assigning a cancer stage status to the sub-set of the plurality of cells.

In some variations, the method may further include obtaining spatially-dependent interferometric images of the plurality of cells; differentiating structural features of the plurality of cells; and reducing interference in the images of sub-cellular metabolic activity of the plurality of cells.

In some variations, automatically assigning the status to the sub-set of the plurality of cells includes submitting the images of sub-cellular metabolic activity of the plurality of cells to a deep learning algorithm, thereby comparing the levels of metabolic activity observed in the sub-set of the plurality of cells to a preselected threshold. In some variations, when the level of metabolic activity is above the preselected threshold, a cell of the sub-set of cells may be assigned a cancerous status.

In some variations, the method may further include automatically assigning a status to the sub-set of the plurality of cells, whereby a region in which the sub-set of the plurality of cells are disposed is annotated as normal or cancerous. In some variations, a sub-set of the structural features from the spatially-dependent interferometric images may be submitted to the deep learning algorithm to thereby assign the status of the region in which the sub-set of the plurality of cells is disposed.

In some variations, assigning the cancer stage status to the sub-set of the plurality of cells may include at least one of determining a level of differentiation of the plurality of cells; determining a level of cellular organization of the plurality of cells; determining a presence of a biomarker; and determining a cancerous/noncancerous region status of other pluralities of cells obtained from the same subject. In some variations, the cancer stage is a y-cancer stage.

In some variations, the time-dependent interferometric images may include a set of images taken over a period of time from about 1 sec to about 5 sec. In some variations, the time-dependent interferometric images may include a set of images taken at a rate from about 50 fps to about 500 fps.

In another aspect, a method is provided for determining the effect of a molecule and/or biological agent upon a cell, including: obtaining images of sub-cellular metabolic activity of a plurality of cells, where the plurality of cells include at least one diseased cell and at least one non-diseased cell, where the images include time-dependent interferometric images; contacting the plurality of cells with a molecule and/or a biological agent; obtaining a plurality of images over a subsequent period of time, where the plurality of images includes sub-cellular metabolic activity of the plurality of cells; and determining an effect of the molecule and/or the biological agent on the at least one diseased cell compared to an effect on the at least one non-diseased cell.

In some variations, the method may further include obtaining spatially-dependent interferometric images of the plurality of cells; differentiating structural features of the plurality of cells; and reducing interference in the images of sub-cellular metabolic activity of the plurality of cells.

In some variations, obtaining the plurality of images over the subsequent period of time may be performed for about 1 hour to about 3 days after contacting the plurality of cells with the molecule and/or the biological agent.

In some variations, determining an effect of the molecule and/or the biological agent on the at least one diseased cell compared to an effect on the at least one non-diseased cell may include determining a level of metabolic activity over the subsequent period of time for the at least one diseased cell and the at least one non-diseased cell.

In some variations, the level of metabolic activity may be increased in the diseased cell relative to the level of metabolic activity in a non-diseased cell. In some variations, the level of metabolic activity may be decreased in the diseased cell relative to the level of metabolic activity in the non-diseased cell.

In some variations, a level of metabolic activity may remain the same for a non-diseased cell.

In some variations, the method may further include identifying an off-target activity of the molecule and/or biological agent upon a non-diseased cell.

In some variations, the molecule may include a biomolecule or an organic molecule. In some variations, the biomolecule may include a protein, nucleic acid, a saccharide, or an expressed product of a cell. In some variations, the organic molecule may include an organic compound having a molecular weight less than about 2000 Da. In some variations, the biological agent may be a virus, a phage, a bacterium or a fungus.

In another aspect, a method is provided for detecting cancerous cells in a set of interferometric images including a spatially-dependent interferometric image and at least one time-dependent interferometric image of a region of tissue including a plurality of cells, including: performing an analysis of the set of images, including: automatically defining regions of the pair of images representing cell boundaries of the plurality of cells; automatically defining regions of the pair of images representing intracellular regions of the plurality of cells; automatically comparing intensities of pixels in the time-dependent interferometric image of an intracellular region of a selected cell of the plurality of cells against intensities of pixels in a region adjacent to the selected cell; automatically assigning the pixel in the intracellular region of the selected cell a status label consisting of deficiently active, normally active or over-active; and summing a plurality of status labels in the intracellular region of the selected cell, thereby defining the cell as healthy or over-active; and defining each over-active cell of the plurality of cells as cancerous.

In some variations, analyzing may be performed by a multi-layered algorithm analysis. In some variations, the pair of interferometric images may be spatially registered.

In some variations, the method may further include determining, from the spatially-dependent interferometric image, that a sub-set of the plurality of cells represent cell types not of interest, thereby eliminating the sub-set of the plurality of cells from further analysis.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a schematic representation of a method for determining the status of a plurality of cells according to some embodiments of the disclosure.

DETAILED DESCRIPTION

As used herein, "sensitivity" of an analysis is a measure of how often the analysis correctly generates a positive test result for samples having the condition tested for, e.g., a "true positive rate". A highly sensitive analysis will not generate many false negatives.

As used herein, "specificity" of an analysis is a measure of how often the analysis successfully generates a negative test result for samples that do not have the condition tested for, e.g., a "true negative rate". A highly specific analysis will not generate many false positive results.

Detection of pathological abnormalities in tissue samples and/or pluralities of cells is a highly specialized and time-consuming effort, usually performed by a select group of clinicians and technical personnel. The costs due to personnel resources and due to delay in time between biopsy procurement and delivery of diagnosis to a patient and/or the physician responsible for determining next steps are high. Further, the analysis performed can be irreproducible from one practitioner to another, relying to some extent on subjective observation and interpretation. In addition, using the standard biopsy practices currently in use, a large percentage of biopsies return to the clinician as incapable of being determined, e.g., undetermined due to inadequacy of the sample for analysis. The lack of usable sample leads to re-order of the biopsy procedure, often causing delay of at least a week, and incurring a second round of expenses for the biopsy team and the patient. Therefore, it would be highly useful to provide a more automatable, consistent and comprehensive method to analyze samples derived from a patient to deliver a rapid, reliable and detailed classification, e.g., diagnosis, of the status of cells present in the patient sample, particularly, but not limited to cancer diagnosis.

Figure 3B:
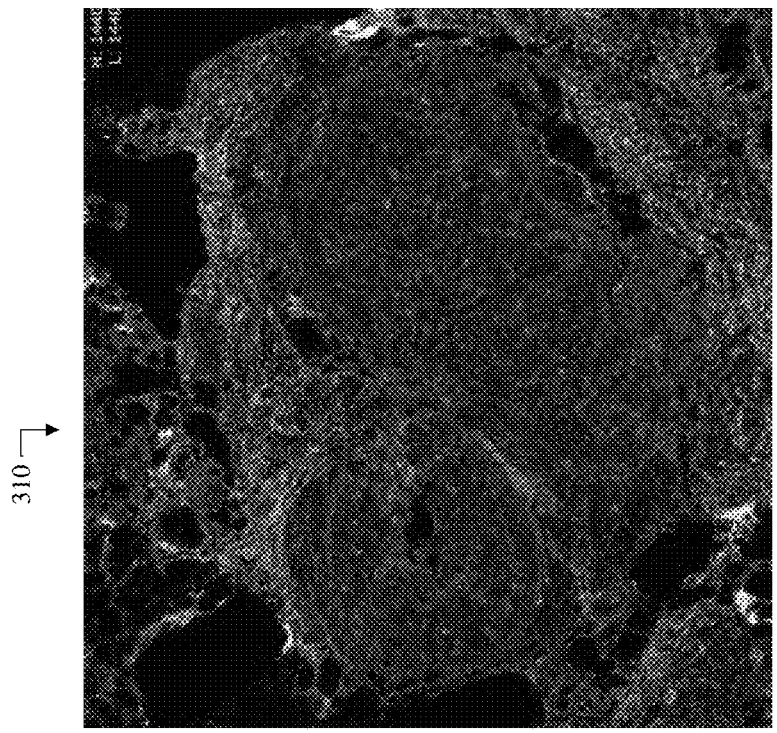
FIG. 3A and FIG. 3B are photographic representations of spatially-dependent interferometric images of a tissue sample according to some embodiments of the disclosure.
Figure 3A:
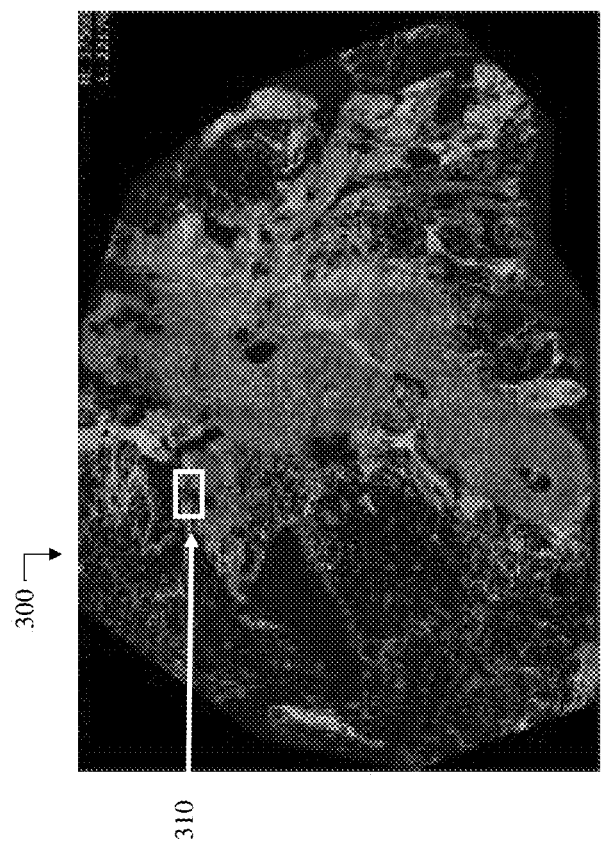

Spatially-dependent interferometry for optical tomography purposes, e.g., techniques using differing reference arm and object arm lengths in the interferometer imaging apparatus, such as Full-Field Optical Coherence Tomography (FF-OCT) has been reported to be useful in cancer diagnosis by revealing structural differences between cancerous and normal tissue, an example of which is shown in FIGS. 3A and 3B. However, the images can be dominated by the strong backscattering signals of, e.g., collagen fibers network or myelinated axons in the brain tissue that hide the weak backscattering signals from cells that are highly transparent. Therefore, additional imaging techniques and methods of processing the data obtained are needed to provide improved cellular imaging to be deployed in tissue biopsy and diagnostics, therapeutics guidance, and novel therapeutics development.

Figure 4B:
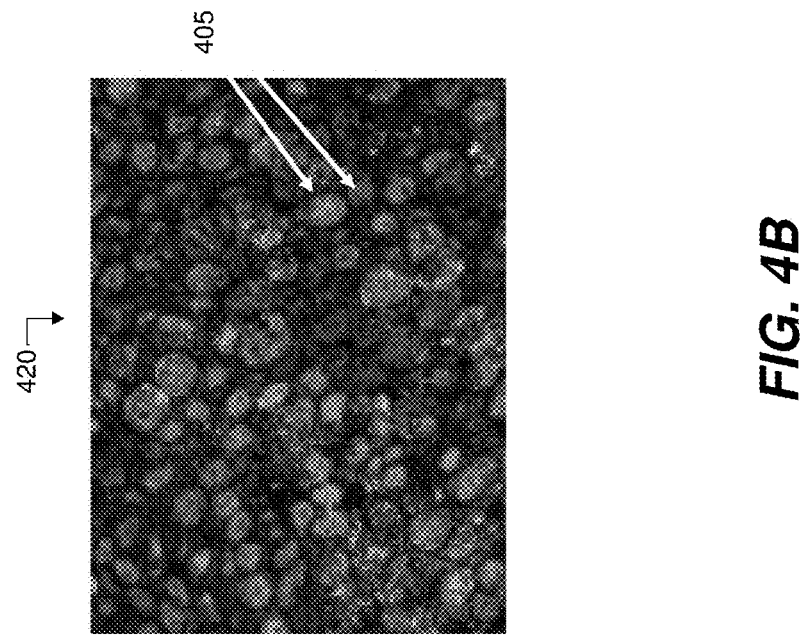
FIG. 4A and FIG. 4B are photographic representations of time-dependent interferometric images according to some embodiments of the disclosure.
Figure 4A:
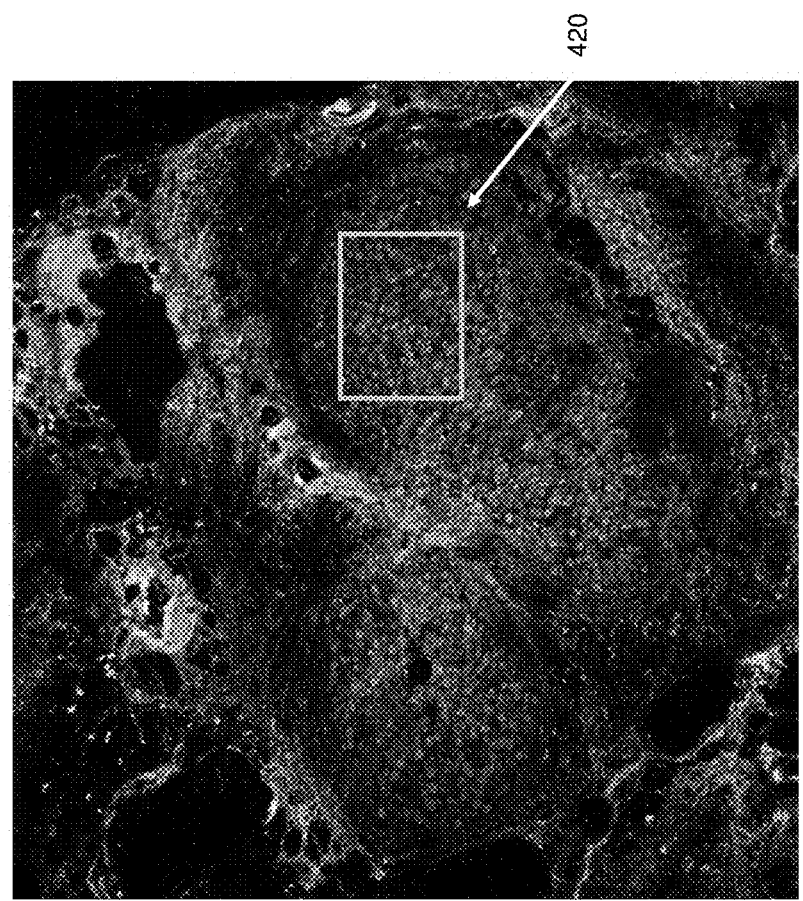

Applicant has discovered that by using interferometric imaging systems configured to changeably adopt selected optical distances (e.g., either different optical distances or the same optical distance) between the reference and sample arms, new image processing methods are possible. The resultant images which can "section" in tissue, e.g., "virtually" scan at different depths within the tissue sample, while reducing and/or eliminating interfering backscattering signals. Importantly, using imaging techniques including more than spatially-dependent interferometric images alone, as described above, more highly resolved and contrasted images of cells may be obtained. Using images acquired with equal reference arm and object arm lengths (e.g., time-dependent interferometric imaging, such as Dynamic Cell Full Field Optical Coherence Tomography (DC-FFOCT), also known as Dynamic Cell Imaging (DCI)), by analyzing and displaying the statistical parameters associated with the time series characteristics for each image pixel along a few seconds (e.g., for a period of time ranging from about 1 second to about 5 seconds and at a rate of acquisition of about 100 frames per sec (fps) to about 500 fps), more detailed information can be analyzed. These improved images can show cellular detail more clearly, including more information about the presence of other cells, e.g., immune cells of various subtypes, size and shape of cells, cellular details such as nuclei and cytoplasm, the percentage of cancerous cells, and the like. Additionally, detail of intracellular metabolism of cells can be obtained, and a metabolic index (MI) computed from the data, permitting precise location of cells exhibiting metabolic activity indicative of cancer, such as shown in FIGS. 4A and 4B.

Further, Applicant has discovered that using a method of analysis combining the data available from both spatially-dependent interferometric images and time-dependent interferometric images leads to a great increase in accuracy of assignment of status of the cells under examination, bringing the level of accuracy nearly equivalent to or even more accurate than human expert diagnosis based on standard hemolysin and eosin (H & E) stain. This increase in accuracy can free the human experts for more involved analyses, and can lower costs, including increasing effectiveness and reproducibility of Rapid On-Site Evaluation (ROSE) during biopsy procedures, at least partially due to large intra-observer and inter-observer discrepancy between cytopathologists evaluating ROSE. In addition, this method can allow ROSE to be performed in an environment where there are no cytopathologists available, thus allowing clinicians to provide better treatment to their patients regardless of geographic location.

These techniques can also be used for therapy guidance after a first therapeutic intervention for a patient, e.g., after a first round of chemotherapy, and to determine the status, including a cancer stage diagnosis, of the patient post-therapy. These methods may also be used to evaluate potential therapeutics, by determining the effect that a putative molecule or biological agent may have on a plurality of cells. The methods described herein may further be used to determine appropriate dosage of therapeutics delivered to patients, based on their unique samples, or alternatively, during a therapeutic drug development process in support of obtaining regulatory approval.

The ability to combine information about (1) structural cell details, e.g., morphology and phenotype, (2) metabolic activity, e.g., cells demonstrating higher than normal metabolic activities which can be classified as cancerous or otherwise diseased, and (3) spatial relationship with respect to each identifiable cell type or phenotype, can be used powerfully to diagnose disease states, identify suitable therapeutic interventions, and evaluate novel therapeutic agents and modalities of treatment. For example, biopsy samples may be analyzed to determine whether an immune cell, such as a T lymphocyte (T cell), dendritic cell (CD), Natural Killer cell (NK) and the like, are present within a sample of cells, within the same region as the diseased, e.g., cancerous, cell. Determining that, for example, T cells are being recruited to the vicinity of the diseased cells may provide guidance on the success of current therapeutic intervention or, in the case, of therapeutic development, that a potential therapeutic agent is capable of enhancing the T cell response.

The methods of image procurement, processing and analysis described herein may be used to replace standard methods of endoscopic biopsy including subsequent frozen section analysis. While methods like Confocal Laser Endomicroscopy (CLE) have been proposed as a real time in vivo assessment tool, such methods are more relevant for identifying lesions for subsequent histologic confirmation. Results from CLE are not capable of a definitive diagnosis; still requiring tissue confirmation.

The methods described herein answer an unmet need. While endoscopic biopsy remains the gold standard for diagnosis of cancers like lung cancer, it requires examination of frozen samples of potentially cancerous tissue required to ensure that adequate, representative (i.e., tumor bearing) tissue was obtained. This is an old technique established in the 1950's, when surgeons demanded intraoperative information on their patients while still in the operating room. Frozen tissue samples are also used to determine whether clean margins have been obtained during a tumor excision, i.e., whether the entire tumor has been removed. It has long been recognized that the information from frozen section diagnosis of cancer is often flawed, with higher misdiagnosis rates than permanent sections which, deleteriously, require at least a day of processing, sectioning, staining, and interpretation. The resultant compromise has been a two-fold solution: today, the most common frozen section diagnosis is 'tissue adequate for diagnosis; final diagnosis deferred for analysis of permanently preserved sections'. That allows the surgeon to close the site of tissue extraction but does not provide other information. It is also somewhat uncertain, leading to performing multiple biopsies until the pathologist is satisfied that adequate tissue has been obtained. Given the inferior histologic appearance of frozen sectioned tissue, definitive diagnosis is often not possible, and certainly dynamic features like cellular character (tumor, immune stromal, etc.) are impossible to assess, and often even to identify with certainty, due to poor image quality.

In contrast, the images obtained as described herein are of very high quality, e.g., low noise, and free of artifacts due to freezing or fixation. The images can, when processed and analyzed using these methods, yield dynamic cell imaging data in three dimensions, which is not true of frozen sections or cytology preps, or CLE and its variants like needle-based Confocal Laser Endomicroscopy (nCLE, Mauna Kea Technologies). The resultant dynamic cell data like shape, size, motility, and relationship to other cellular and tissue constituents in viable cells at high resolution has not been available from any other method. For example, broad use of immunoncology agents like PD1 and CTLA inhibitors has placed a premium on identification of the immune cell repertoire in and around a patient's tumor.

The methods of analysis and diagnosis described herein may be able to address this unmet need in real time, in ways that are impossible with stained tissue sections, as mentioned, and which are beyond the capability of liquid biopsies. Liquid biopsies, while intended to provide such information, compete with high background 'noise' from non-tumor contributions to the signal, and lose spatial relationships, neither of which is true of the methods described herein.

However, the use of the image procurement and processing methods described herein do not preclude subsequent use of ROSE methods. On the contrary, the instant methods can improve ROSE as currently practiced, and may provide a better alternative. In such cases, because the imaging methods described herein do not alter the tissue sample, high quality tissue samples are still available for additional studies. This is not true of cytology preps or frozen sections subsequently fixed in formalin. CLE methods further limit subsequent studies because there is no tissue for evaluation. For all these reasons, the methods as described herein can be interposed between the procedure and any subsequent tissue processing, and may enable virtually unlimited opportunities for subsequent tumor characterization. For example, in the genomic profiling of tumors, a portion of the biopsied tissue must be set aside to avoid performing the assay on markedly inferior formalin fixed, paraffin embedded (FFPE) tissue, thereby reducing the amount of tissue remaining for other analysis. When using the methods described herein, on the other hand, the entire tissue sample remains viable after imaging and analysis, and the most representative areas for further analysis are readily identified due to the high quality of the FF-OCT images.

The methods described herein therefore may offer a dramatic enhancement of the information that can be obtained from a biopsy of any kind (particularly from small tissue samples obtained via minimally invasive biopsies), in real time, without destroying any portion of the specimen or compromising a subsequent detailed analysis like DNA sequencing or protein analysis, increasingly common in cancer patient management. The methods described herein may have the potential to provide critically important information not available by any other means. Some examples include non-tumor cellular infiltrate, a parameter of increasing interest, as it predicts patient response to expensive immunoncology therapy and tumor cell distribution within the biopsy. This is critically important in cancer surgery. Surgeons will often take a large enough biopsy of tissue in the tumor bed to document 'clean margins' with normal tissue around the tumor, and thus complete tumor excision; positive margins indicate inadequate surgical excision and the need for additional tissue removal. Unfortunately, a frozen section (or even a permanent section produced by the next day) is a two-dimensional assay of a three-dimensional tissue, where the tumor may have extended to and beyond the tissue margins. As a result, the actual clinical scenario is only revealed when the patient's tumor recurs locally, definitive evidence that it was not all removed. The ability to image specimens in three dimensions and identify tumor cells may be an invaluable adjunct to surgical margin analysis and detection of residual tumor. Yet another example of may be for so-called PDX (patient derived xenograft) use. Pharma and biotech companies increasingly rely on human tumors directly implanted in a permissive host (the PDX xenografts) to more realistically assess response to various targeted therapies. PDX tissue is scarce, because most biopsies are either frozen or fixed (which kills the tissue cells) and renders them useless for this purpose. As viable, validated tumor tissue (which the present methods can non-destructively identify) becomes more widely available after biopsy, the methods described herein may be used to identify therapy most likely to benefit the patient, instead of the current method of prediction based on tumor markers and other indirect measures which often fail to predict response.

Methods of Imaging and Classifying Cells: Deep Learning Analysis Methods.

As mentioned above, a combination of the data contained within a spatially-dependent interferometric (FF-OCT) image and a time-dependent interferometric (DCI) image, obtained using a system like system 200, described below, can provide much more detailed information about the state of a region of cells, whether it is used for diagnosis, e.g., from a biopsy sample, or for screening type assays, e.g., from a plurality of cells, as shown in FIG. 1A. The FF-OCT image 110 and the DCI image 120 may be spatially registered for the plurality of cells under analysis.

Figures 4C, 4D:
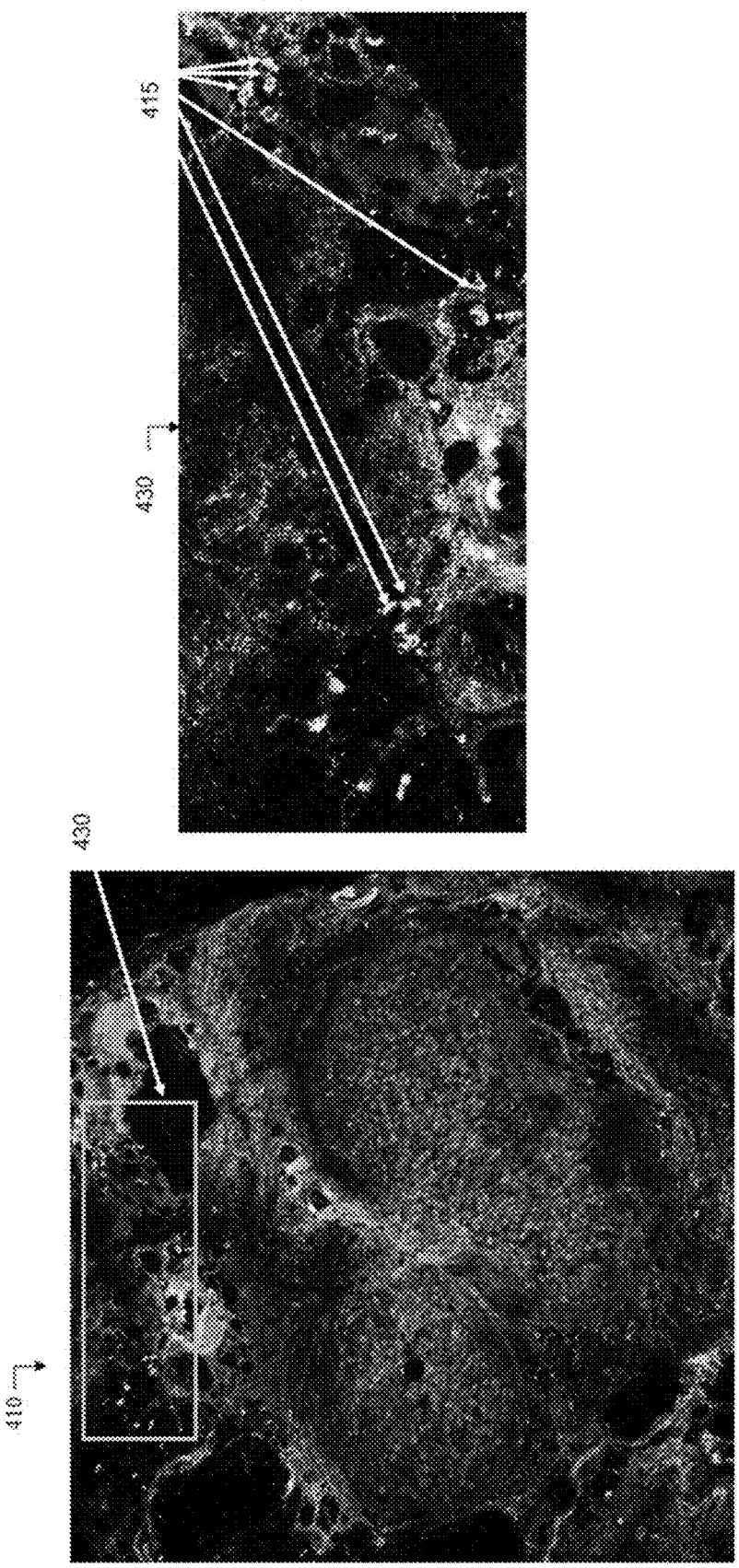
FIG. 4C and FIG. 4D are photographic representations of time-dependent interferometric images according to some embodiments of the disclosure.
Figure 4E:
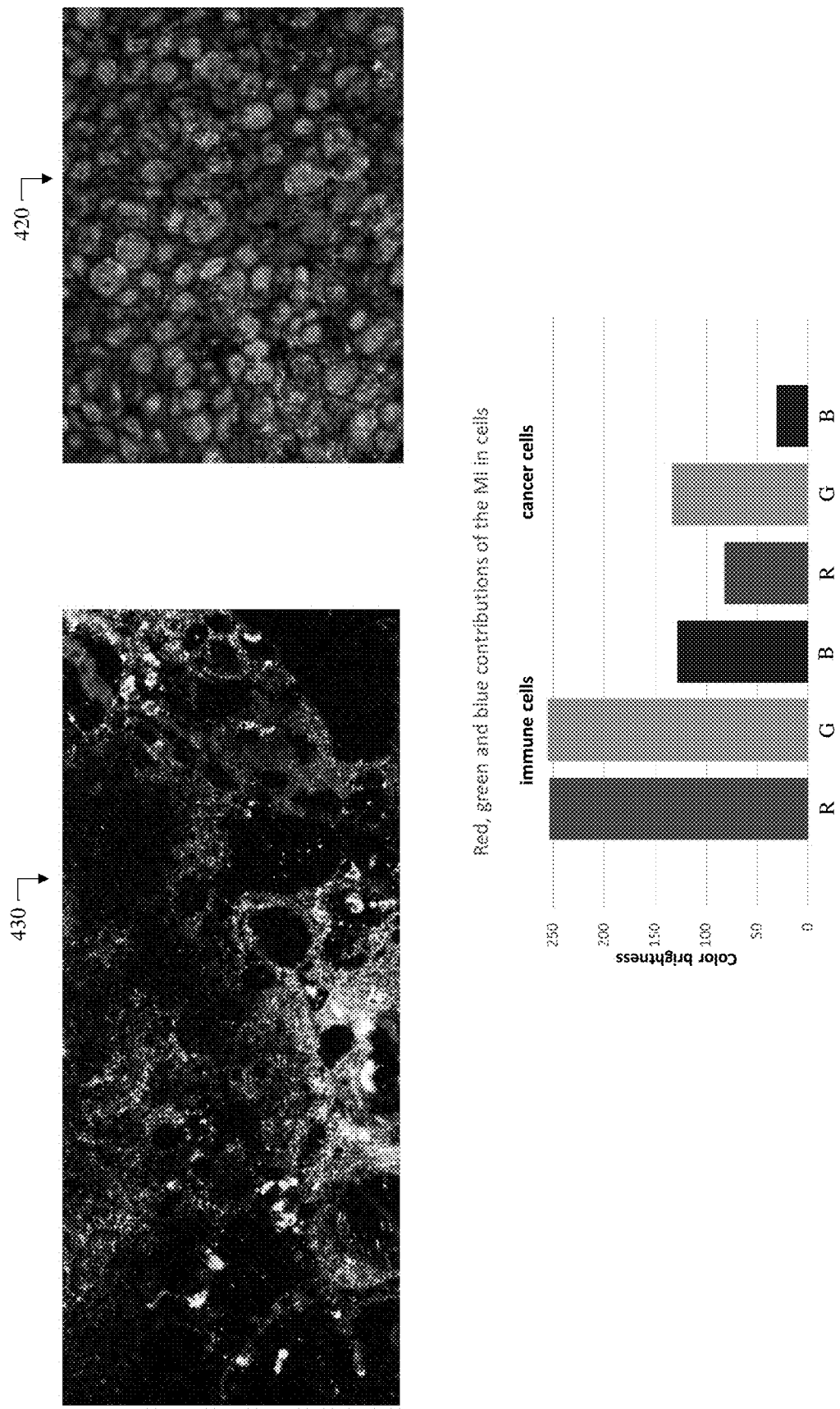
FIG. 4E shows the photographic representations of selected regions from FIG. 4B and FIG. 4D and a graphical representation of metabolic index coding for elements of the selected regions.

As shown in FIG. 3A, a spatially-dependent interferometric image 300 (FF-OCT image) shows structural details of the sample, and region 310 is a small portion of image 300. FIG. 3B shows image 310 of that region, enlarged. FIG. 4A shows a time-dependent interferometric image 410, (DCI image) which is the same region as that shown in region 310. FIG. 4A has been processed as described herein, to produce a colorimetric Metabolic Index (MI) image, which in this case, has cells coded to the Red, Green and Blue channels according to the metabolism speed (with respect to color) and level of activity (with respect to brightness). Briefly, the MI display will appear brighter if metabolism of the cell is more active and redder if metabolism speed is greater. Sub-region 420 within FIG. 4A is enlarged and presented in FIG. 4B, where details of individual cancer cells 405 are more readily apparent. In image representations of this type, the color gradation from blue to green to red defines increasing rankings of movement, e.g., faster metabolic activity, and the brightness of the pixel represents greater intensity of activity. FIG. 4C shows the same region 410 as that of FIG. 4A, differing in that sub-region 430 is selected. FIG. 4D shows region 430 enlarged, where details of individual immune cells 415 are more readily apparent. FIG. 4E compares the metabolic index between cancer cells 405 and immune cells 415 regions 420 and 430 respectively, showing that each cell type has a different color brightness distribution per color (e.g., red (R), green (G), blue (B)) and therefore may be differentiated.

Figure 1B:
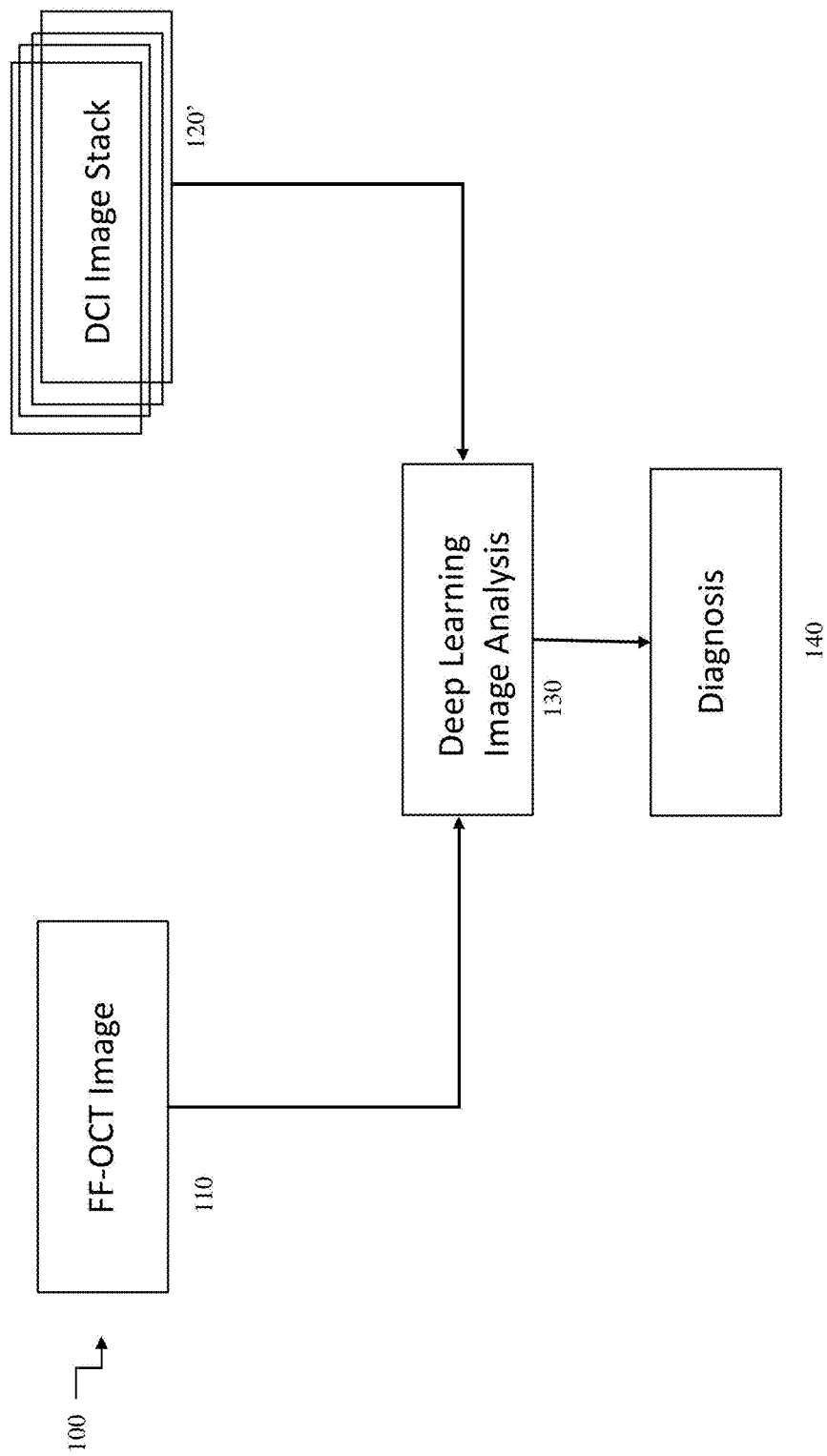
FIG. 1B is a schematic representation of a method for determining the status of a plurality of cells according to some embodiments of the disclosure.

In other embodiments, a variation of this analysis can be performed, as shown in FIG. 1B. As described above the color representation, e.g., MI, can confer visual information to a user looking at the images, and can be used for the deep learning assisted analysis for diagnosis. However, much more data is contained within the time series than what the MI color representation infers. In the variation shown in FIG. 1B, the deep learning analysis may be provided with all the data contained in the data cube (including coordinates and time) associated with the series of time-dependent images, e.g., a DCI Image stack 120', which may have any number n of images therein, where n may be from about 2 to about $10^3$ images, or about 10 to about $10^6$ images. Since DCI images may also be acquired at varying depths, the entire thickness of a sample may be probed.

In any case, deep learning analysis 130 of images 110 and 120 can extract and classify the combined data from each pixel of each spatially registered image, leading to heightened detail and improved accuracy of diagnostics, without relying upon laborious and highly specialized human visual analysis. A more accurate diagnosis 140 may be obtained. Thus, these methods can increase speed, accuracy and decrease workflow dependencies upon highly skilled clinicians, freeing them for other higher level analyses.

Deep learning is a class of machine learning algorithms employing multiple layers to progressively extract higher level features from the raw input. The term "deep" as used in deep learning comes from the use of multiple layers in the network. The network may have any number of layers of bounded size, which permits practical application and optimized implementation, e.g., requiring significantly decreased computing resources and computing time. The layers may also be heterogeneous and may deviate widely from biologically informed models. The deep learning method may be a supervised, semi-supervised or unsupervised machine learning method. The deep learning methods, as used herein, may include any of the variety of architectures such as deep neural networks, deep belief networks, recurrent neural networks and convolutional neural networks as known in the art, which may lead to analysis results, which can surpass human expert performance. The deep learning analysis method may be a convolutional neural network (CNN), and in some variations, is a pretrained CNN. The CNN may be any suitable CNN, and may be, but is not limited to AlexNet, VGG16, VGG19, SqueezeNet, GoogLeNet, Inception v3, DenseNet-201, MobileNetV2, ResNet-18, ResNet-50, ResNet-101, Xception, InceptionResNetV2, NASNet-Large, NASNet-Mobile, ShuffleNet and the like. In some embodiments, the deep learning analysis method may be AlexNet, GoogLeNet, ResNet-101, or ShuffleNet. The deep learning analysis may automatically assign a status to at least one cell of the plurality of cells.

In some variations, the deep learning method may be a method of determining the status of a plurality of cells, e.g., a cancer status, where the plurality of cells may be suspected to comprise a cancerous cell. The status may be automatically assigned and is selected from a normal cell status or a cancerous cell status, for individual cells, a plurality of cells, or a region containing the plurality of cells. In some variations, determining whether a plurality of cells is cancerous may further include determining a stage for the cancerous cells. In some embodiments, determining the stage of the cells may include determining the y-stage, e.g., the method is performed upon a sample of cells from a patient already treated with a first type of cancer therapy.

In other variations, the deep learning method may be a method of determining the effect of a molecule or biological agent upon a plurality of cells, which may include both diseased cells and non-diseased cells. For example, at least some of the plurality of cells may have a viral infection, a bacterial infection, a metabolic dysfunction, a secretory function or the like. Upon treatment with the molecule or biological agent, the effect of the molecule/biological agent may be analyzed to determine whether the diseased cells have recovered to a non-diseased status; have been eliminated, e.g., inactivated, to prevent further disease spread; whether the non-diseased cells have maintained a non-diseased status; or whether the non-diseased cells have been deleteriously affected by the molecule/biological agent, e.g., off-target effects. The outcome of the analysis, e.g., diagnosis 140, may include any of these determinations. For example, a plurality of cells including one or more cancerous cells may be contacted with a molecule or biological agent which may target cancerous cells for killing. The images obtained over a selected period of time may be submitted to the deep learning method to determine whether the molecule/biological agent is effective at killing cancerous cells. As the cancerous cell(s) are killed, the metabolic activity of such cell(s) is reduced, then disappears, which can be identified by the deep learning analysis. In other applications, such as evaluation of potential anti-viral agents, cells infected by virus may have an increased rate of metabolism due to viral replication. After contacting a plurality of cells with a molecule/biological agent, the images obtained over a selected time post administration may be submitted to deep learning analysis. The analysis can determine whether cells observed to be infected demonstrate reduction of metabolic activity to levels of metabolism associated with non-diseased cells, e.g., viral infection has been reduced or eliminated. Alternatively, the analysis can determine whether the cells observed to be infected prior to administration of the molecule/biological agent are killed, e.g., the cell demonstrates no metabolic activity. Further, the analysis can determine whether administration of the molecule/biological agent prevents additional cells, e.g., adjacent cells, from becoming newly infected. For example, adjacent cell(s) may demonstrate increased metabolic activity over the post-administration imaging period, which can indicate newly infected cells.

The multi-layer algorithm analysis may analyze and classify a wide variety of features. The features may be extracted from the algorithmic analysis, e.g., resulting from the analysis, or the features may be extracted from pre-processing of the images. When features are extracted from pre-processing, they are derived from metrics calculated before algorithmic analysis, with subsequent classification of the metrics or grouping of the metrics by the algorithmic analysis to better separate and segment the dataset. Any suitable set of features may be used within the method. In some analyses, where a diagnosis with regard to diagnosing whether a region of cells is cancerous, features used within the deep learning analysis may determine increases in the local cell density, a range in number of cells per unit volume/area, the number of mitotic cells (e.g., having modified area and geometry), cell motility, increase in backscattered signal in cancerous cells, possibly due to an increased trafficking to support faster growth of unregulated cancerous cells, modification to extracellular matrix, and/or collagen fibers (e.g., evidence of more disorganized environments compared to healthy tissue). In other applications, such as determining the effect that a molecule or a biological agent may have upon cells, similar features may also be used as part of the deep learning method. In the latter types of analyses, a determination of extent of cell death over the period of image capture may also be included, as a feature.

In some variations, the method may further include training the multi-layered algorithm analysis where a portion of data from the time-dependent interferometric image and/or a portion of data from the spatially-dependent interferometric image may be used to train the deep learning method. In some variations, the training may be based on expert analysis. The portion of data reserved for training an untrained algorithm may be about 20%, about 30%, about 33%, about 40%, about 45%, about 50%, or any percentage therebetween of the total amount of data.

Figure 5:
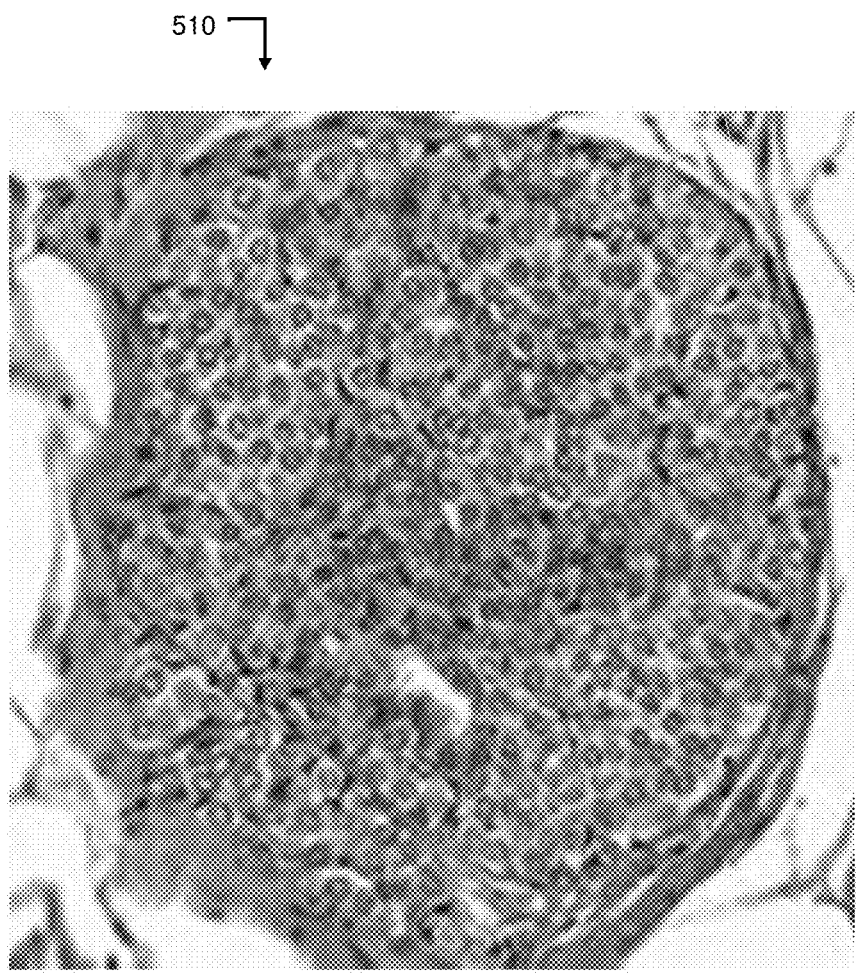
FIG. 5 is a photographic representation of a time-dependent image according to some embodiments of the disclosure.

In some other variations, the deep learning method may also include submitting an image of the plurality of cells, which may include labelling with a detectable label, which may be colorimetric, radiometric, fluorescent, or the like. For example, the labelling may be hematoxylin and eosin (H&E), which label nucleic acids and proteins within a cell, an example of which is shown in FIG. 5. H & E stained image 410 is the same region of cells as region 310, 410 of FIGS. 3A-B and 4A-B. In some other examples, a dye such as Sirius Red (Sigma Aldrich Cat. No. 365548) may be used to image collagen and analyze for fiber orientation and density. In other non-limiting examples, any cell surface marker may be labeled, e.g., such as programmed death-ligand 1 (PD-L1), which can assist in diagnosis and/or guiding anti-cancer therapy or determining efficacy of a molecule/biological agent. The deep learning method may combine data derived from such labelling to further analyze and classify the cells in the image.

In some other variations, the deep learning method may further include differentiating structural features of the plurality of cells; and reducing interference in the time-dependent interferometric image of the plurality of cells.

Methods of Imaging and Classifying Sub-Cellular Metabolic Activity: Machine Learning Analysis Methods.

Figure 7:
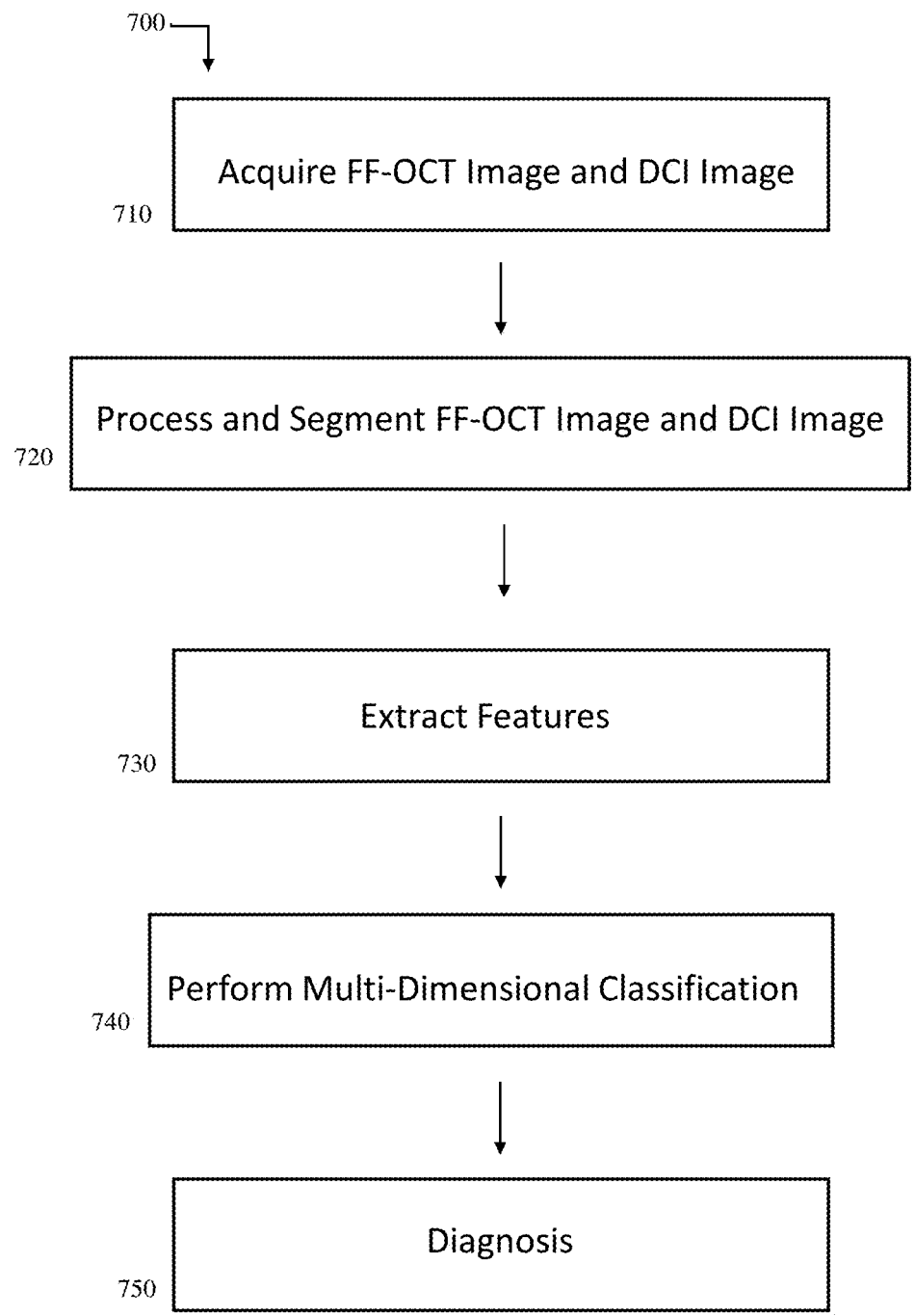
FIG. 7 is a schematic representation of a method for classification of cells.

The method 700, as shown in FIG. 7 of imaging and classification, concluding in diagnosis, as shown in box 750, includes obtaining images of one or more regions of a tissue sample or a plurality of cells. The images may have an isotropic resolution of about 1 micron to about 5 microns. In some variations, the images may have a resolution of about 1 micron. For each region or field of view (FOV), at least one spatially-dependent interferometric (FF-OCT) image and at least one time-dependent interferometric (DCI) image is obtained, as shown at box 710.

The images may then be analyzed to define cells, e.g., segmented from other features visible in the image, as shown in box 720. A machine-learning segmentation software may be used, such as ilastik, an open source image classification tool (ilastik.github.io), which is based on random forest classifiers. Labels are manually drawn on the DCI images in a user interface. Each pixel neighborhood may be characterized by a set of generic nonlinear spatial transformations applied to each channel (R, G, or B) of the DCI image. Image transformations may be selected empirically or using pre-determined values, to obtain images having the best contrast.

A similar processing and segmentation is performed for the spatially-dependent interferometric (FF-OCT) image of each FOV, using gray scale images. The process may be performed to identify and extract fiber-type structural features from the image of the tissue. The classes to be identified and segmented are fibers, between fibers, and cells.

Based on the previous segmentation, general features can be extracted from individual ROIs as metrics to classify a sample (per individual field of view) as normal or pathological, as shown in box 730. For example, cancer is a disease arising from loss of control of cell division and reproduction processes, leading to uncontrolled growth. What may be observed are increases in the local cell density, the number of cells, the number of mitotic cells (with modified area and geometry), cell motility, increase in backscattered signal in cancerous cells, possibly due to an increased trafficking to support the faster growth. As a consequence, the local environment may be modified, including the extracellular matrix, and collagen fibers, and often shows more disorganized environments compared to healthy tissue.

Multi-dimensional classification may also be included, as shown at box 740. In order to increase performance, machine-learning classifiers in multidimensional space may be applied to permit comparison with a variety of algorithms. For example, Matlab Toolbox Classification Learner of MATLAB®, that allows comparing between many algorithms. In some variations, the linear SVM (Support Vector Machine) may be selected to for the analysis. New examples are assigned to one category or the other, when used as a non-probabilistic binary linear classifier, but SVM may also be used in a probabilistic classification mode. As features, combinations of FF-OCT and DCI features may be used, and may include both mean and STD of values for each image when several values were obtained (e.g., for cell diameter). The analysis may include an externally assigned phenotype, e.g., histology assignment on each tissue.

Accordingly, in some embodiments, a method is provided for detecting cancerous cells in a pair of interferometric images comprising a spatially-dependent interferometric image and a time-dependent interferometric image of a region of tissue comprising a plurality of cells, including: defining regions of the pair of images representing cell boundaries of the plurality of cells; defining regions of the pair of images representing intracellular regions of the plurality of cells; automatically comparing intensities of pixels in the time-dependent interferometric image of an intracellular region of a selected cell of the plurality of cells against intensities of pixels in a region adjacent to the selected cell; automatically assigning the pixel in the intracellular region of the selected cell a status label consisting of deficiently active, normally active or over-active; summing a plurality of status labels in the intracellular region of the selected cell, thereby defining the cell as healthy or over-active; and defining each over-active cell of the plurality of cells as cancerous. In some variations, the pair of interferometric images may be spatially registered. In some variations, the method may further include determining, from the spatially-dependent interferometric image, that a sub-set of the plurality of cells represent cell types not of interest, and the sub-set of the plurality of cells may be eliminated from further analysis.

Improved Biopsy Methods.

Figure 6A:
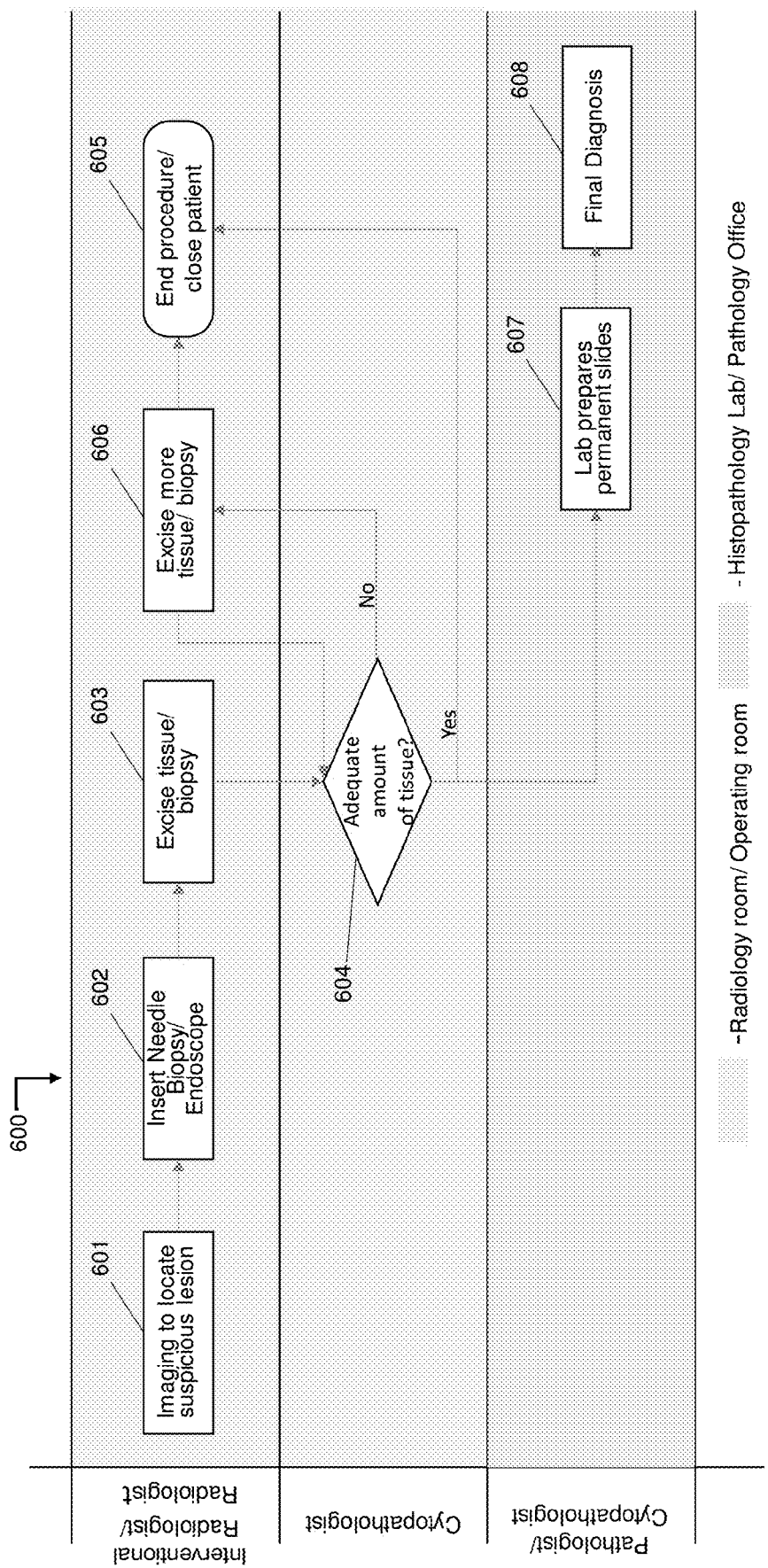
FIG. 6A is a schematic representation of a biopsy procedure currently available.

Rapid On-Site Evaluation (ROSE) is one method for improving the likelihood that sufficient and clinically relevant biopsy samples are obtained, and a schematic of the typical current workflow 600 is shown in FIG. 6A. The steps performed in the top two rows are typically performed in a radiology room or operating room, and the steps in the bottom row are typically performed in a histopathology lab and/or pathology office. As currently practiced, imaging is performed at step 601 to guide the tissue extraction. The imaging may be contrast optical imaging, label-free optical imaging, radiotopic imaging, ultrasound imaging or magnetic imaging. At step 602, the biopsy needle may be guided or steered with an endoscope to the site where disease is suspected, and tissue is excised at step 603. The sample is transferred to a cytopathologist, who examines the sample and determines, at step 604 while the patient is still in the biopsy procedural theater, whether enough cells are present and whether those cells are representative of the tissue prompting the need for biopsy. While the cytopathologist is performing this analysis, the patient is still held in the procedural theater, waiting for a decision from the cytopathologist. If sufficient and representative cells are present, the biopsy procedure is ended at step 605 and closure of the biopsy site may be performed. If insufficient and/or non-representative cells are found in the sample, then the Interventional Radiobiologist or Radiologist returns to the patient and excises more tissue at step 606 in an additional excision, which is joined with the first obtained sample to form a sufficiently large and representative sample. Only then is biopsy procedure concluded, the patient released and the biopsy procedural theater freed for the next patient. The biopsy sample (or combined biopsy samples) are then transfer to a Pathologist or Cytopathologist to prepare slides at step 607 and from there, derive a final diagnosis for the patient at step 608. However, this involves cytopathologists at two points in the process. Therefore, while ROSE is currently shown to provide higher yield of adequate final diagnosis, it is not widely performed due to lack of available cytopathologist resources. Additionally, results of cytopathologists are also subjective and prone to inter- and intra-observer variability. ROSE methods that incorporate and rely on indirect tools like CLE may also be prone to false positives and false negatives because of their subjective nature, and additionally, do not themselves provide tissue specimens for definitive downstream analysis.

Figure 6B:
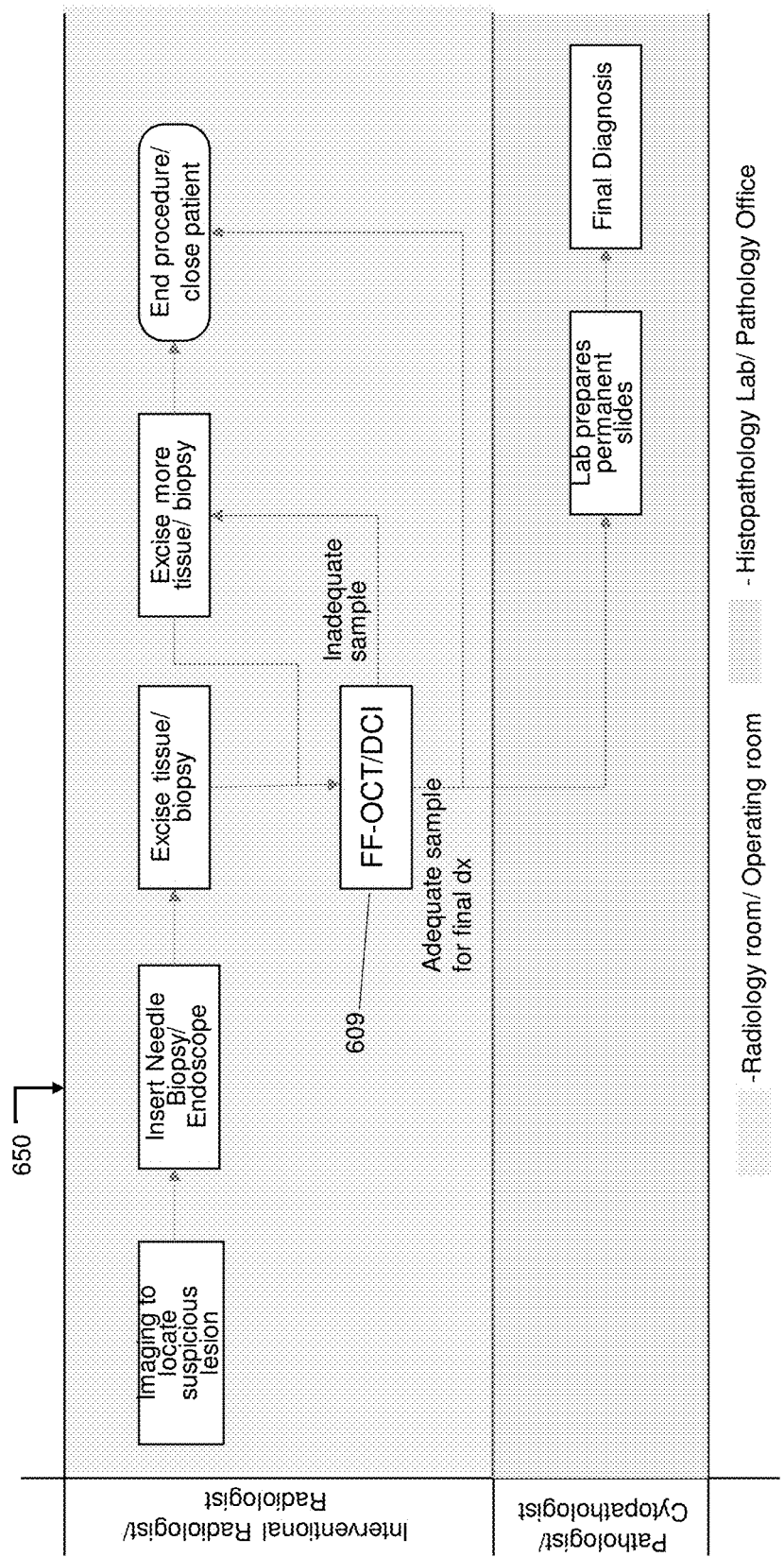
FIG. 6B is a schematic representation of a biopsy procedure according to some embodiments of the disclosure.

In contrast, Radiologists and Intervention Radiologists can perform biopsies without the need to rely on cytopathologists and cytotechnicians to perform ROSE, when DCI and or FF-OCT imaging, as described herein, is used, at the point of biopsy, as shown in workflow 650 of FIG. 6B. The steps shown in the top row in the top row are performed by an interventional radiologist or radiologist in the radiology room or operating room, and the steps in the bottom row are performed by a pathologist or cytopathologist in a histopathology lab and/or pathology office. Immediate analysis of the excised material using DCI and/or FF-OCT imaging at step 609 can be made right in the biopsy procedural theater, decreasing the amount of time needed per patient in the procedural theater, removing the cost and time commitment of a Pathologist/Cytopathologist, and even enabling the Pathologist/Cytopathologist to be remote from the clinic where the biopsy is taken.

Accordingly, a method is provided for performing a biopsy on a subject in need thereof, comprising: imaging a region of tissue to identify a region of interest; inserting a biopsy needle into the region of interest; excising a first tissue sample from the region of interest; obtaining a set of time-dependent interferometric images and a spatially-dependent interferometric image of the first tissue sample; and determining a number of cells of interest present within the first tissue sample. Imaging the region of tissue may include contrast optical imaging, label-free optical imaging, radiotopic imaging, ultrasound imaging or magnetic imaging. In some embodiments, inserting a biopsy needle may include guided insertion. In some embodiments, determining a number of cells of interest may include a quantified number of cells of interest. In other embodiments, determining a number of cells of interest may include estimating the number of cells or may include annotating a plurality of cells without counting the number of cells present.

Imaging the region of tissue, inserting the biopsy needle, excising the first tissue sample, obtaining the set of time-dependent interferometric images and the spatially-dependent interferometric image, and determining the number of cells of interest present may be performed within the biopsy procedural theater.

Obtaining the set of time-dependent interferometric images and spatially-dependent image may further include processing the images to obtain images of sub-cellular metabolic activity of a plurality of cells within the first tissue sample.

The method may further include assigning a status to one or more cells of the plurality of cells, wherein the one or more cells having the assigned status is a cell of interest. The assigned status may be a diseased cell status. In some embodiments, the diseased cell status may be a cancerous cell status. In other embodiments, the assigned status may be identifying a cell type, such as an immune cell such as, but not limited to T cells, NK cells, and the like.

Determining a number of cells of interest may include submitting the images of sub-cellular metabolic activity to processing by a multi-layer algorithm, thereby assigning the status to the one or more cells. Assigning the status to the one or more cells may include comparing a level of metabolic activity observed in the one or more cells to a preselected threshold.

The method may further include obtaining a second tissue sample from the region of interest, when the number of cells of interest in the first tissue sample is insufficient for analysis.

Methods of Analyzing Molecule/Biological Agent Effect on Cells.

The methods of analyzing images from DCI and/or FF-OCT images may be used to determine the effects of a molecule and/or a biological agent upon a plurality of cells. In particular, the effect of the molecule and/or biological agent may be performed on a mixture of diseased and non-diseased cells. The plurality of cells may further include more than one kind of cell, so that off-target effects of a therapeutic on other types of cells normally found near the type of diseased cell may be identified early.

The plurality of cells may be held in an imaging vessel permitting maintenance of the cells, for example, exchange of medium, exchange of gaseous environment, and addition of nutrients. A series of time-dependent interferometric (DCI) images may be obtained over a period of time to observe the effect of the molecule and/or a biological agent, and the images processed to provide a metabolic index (MI) image showing coded high, medium and low intracellular activities. The effect of the molecule and/or a biological agent can be compared between the diseased cell and the non-diseased cell to determine whether the molecule and/or a biological agent is effective in treating the disease of the diseased cell. For example, at least some of the plurality of cells may have a viral infection, a bacterial infection, a metabolic dysfunction, a secretory function or the like. Upon treatment with the molecule or biological agent, the effect of the molecule/biological agent may be analyzed to determine whether the diseased cells have recovered to a non-diseased status; have been eliminated, e.g., inactivated, to prevent further disease spread; whether the non-diseased cells have maintained a non-diseased status; or whether the non-diseased cells have been deleteriously affected by the molecule/biological agent, e.g., off-target effects. A number of disease states, such as cancer and viral infections, diseased cells may have a higher level of intracellular metabolic activity which can be imaged as described herein, and the analysis may determine whether the level of metabolic activity in a diseased cell decreases upon being contacted with the molecule and/or biological agent, relative to that of a non-diseased cell. The analysis may also permit the observation whether the molecule and/or biological agent adversely affects the metabolic activity of the non-diseased, e.g. reduces or obliterates metabolic activity such as may be seen with off-target activity of the molecule and/or biological agent.

For example, a plurality of cells including one or more cancerous cells may be contacted with a molecule or biological agent which may target cancerous cells for killing. Images obtained as described herein over a selected period of time post-administration may be analyzed to determine whether the molecule/biological agent is effective at killing cancerous cells. As the cancerous cell(s) are killed, the metabolic activity of such cell(s) is reduced, then disappears, which can be identified in the series of images. In other applications, such as evaluation of potential anti-viral agents, cells infected by virus may have an increased rate of metabolism due to viral replication. After contacting a plurality of cells with a molecule/biological agent, the images obtained over a selected time post administration may be analyzed to determine whether cells observed to be infected demonstrate reduction of metabolic activity to levels of metabolism associated with non-diseased cells, e.g., viral infection has been reduced or eliminated. Alternatively, the analysis can determine whether the cells observed to be infected prior to administration of the molecule/biological agent are killed, e.g., the cell demonstrates no metabolic activity. Further, the analysis can determine whether administration of the molecule/biological agent prevents additional cells, e.g., adjacent cells, from becoming newly infected. For example, adjacent cell(s) may demonstrate increased metabolic activity over the post-administration imaging period, which can indicate newly infected cells.

This method can be used for guiding therapy for a patient who already had completed a first course of treatment, to identify a suitable next therapeutic. The method may be used to screen or assay therapeutic agents during discovery or development in pre-clinical studies.

The period of observation during which imaging occurs may be about 1 hour, about 4 hours, about 8 hours, about 12 hours, about 24 hours, about 36 hours, about 48 hours, about 72 hours or more.

In some variations, spatially-dependent interferometric images may be obtained, and structural details of the plurality of cells may be differentiated from intracellular details. The effect of the structural details may be used to further modify the time-dependent interferometric image to remove interferences and provide clearer images of sub-cellular metabolic activity of the plurality of cells.

The molecule may be a biomolecule or an organic molecule. In some variations, the biomolecule may be a protein, nucleic acid, a saccharide, or an expressed product of a cell. In some variations, the organic molecule may be an organic compound having a molecular weight less than about 2000 Da. In some other variations, the biological agent may be a virus, a phage, a bacterium or a fungus.

Imaging System and Methods of Image Processing.

Figure 2:
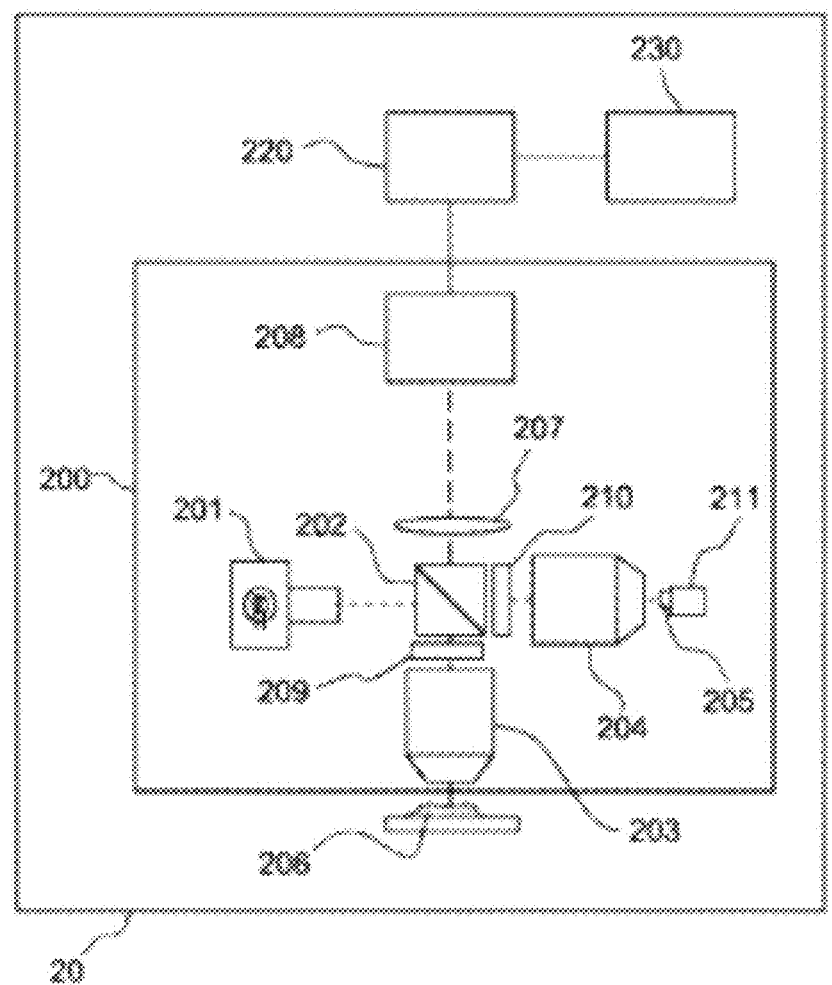
FIG. 2 is a schematic representation of an imaging system for use in the methods according to some embodiments of the disclosure.

An embodiment of an imaging system 20 suitable for implementing the methods according to the present description is schematically represented in FIG. 2.

The imaging system 20 comprises an interference device 200, an acquisition device 208 and at least one processing unit 220.

The interference device 200 is adapted to produce optical interferences between, on the one hand, reference waves obtained by reflection of the light emitted by a light source 201, spatially incoherent and of low coherence length, by each elementary surface of a reflection surface 205 of a reference arm of the interference device and, on the other hand, of the object waves obtained by backscattering of the light emitted by the same source by each voxel of a slice of a sample 206 depthwise in the sample, the sample 206 being disposed on an object arm of the interference device, said voxel and said elementary surface corresponding to the same point of the imaging field.

The light source 201 is a source that is temporally incoherent or of low coherence length (in practice, in a range from 1 to 20 micrometers) and spatially incoherent, for example a halogen lamp or an LED. According to one or more exemplary embodiments, the light source 201 can form part of the imaging system 20, as in the example of FIG. 2, or can be an element external to the imaging system, the imaging system being adapted to work with light waves emitted by the source.

The acquisition device 208 allows the acquisition of at least one two-dimensional interferometric signal resulting from the interferences between the reference waves and the object waves.

The processing unit 220 is configured to execute at least one step of processing of at least one two-dimensional interferometric signal acquired by the acquisition device 208 and/or at least one step of image generation in accordance with at least one of the imaging methods according to the present description, in order to generate at least one image of the sample slice.

In one embodiment, the processing unit 220 is a computing device that may include a first memory CM1 (not represented) for the storage of digital images, a second memory CM2 (not represented) for the storage of program instructions and a data processor, capable of executing program instructions stored in this second memory CM2, in particular to control the execution of at least one step of processing of at least one two-dimensional interferometric signal acquired by the acquisition device 208 and/or of at least one step of image computation in accordance with at least one of the imaging methods as described herein.

The processing unit can also be produced in integrated circuit form, comprising electronic components suitable for implementing the function or functions described in this document for the processing unit. The processing unit 220 can also be implemented by one or more physically distinct devices.

The acquisition device 208 may be, for example, an image sensor such as a CCD (Charge-Coupled Device) or CMOS (Complementarity metal-oxide-semiconductor) camera type. This acquisition device is capable of acquiring images at a high rate, for example with a frequency of 100 Hz. Depending on the dynamics of the sample studied, and more specifically the dynamics of the movements within the sample, it will be possible to use the cameras operating from a few Hz up to several KHz.

According to one embodiment, the interferometer 200 comprises a beam-splitter element 202, for example a non-polarizing splitter cube, making it possible to form two arms. In one of the arms, which will hereinafter be called "reference arm" there is the reflection surface 205, flat, for example a mirror. The other arm, which will hereinafter be called "object arm", is intended to receive, in operation, the three-dimensional diffusing sample 206, of a slice of which there is a desire to produce a tomographic image at least one depth according to one of the methods of the present description.

In the example of FIG. 2, the interferometer is of Linnik interferometer type and comprises two identical microscope lenses 203, 204 arranged on each of the arms. The reflection surface 205 is thus located at the focus of the lens 204 of the reference arm, and the sample 206 is intended to be positioned at the focus of the lens 203 of the object arm. Other types of interferometers can be envisaged for the implementation of the methods according to the present description, and in particular interferometers of Michelson, Mirau, Fizeau and other such types.

At the output of the interferometer 200 there is an optic 207, for example an achromatic doublet, whose focal length is adapted to allow a suitable sampling of the sample 206 by the acquisition device 208, and which makes it possible to conjugate the planes situated at the foci of the two lenses in one and the same plane at the output of the interference device. The acquisition device 208 is placed in the latter plane in order to acquire the interference signals produced by the interference device. In order to not limit the resolution permitted by the microscope lenses 203 and 204, the choice of the focal length of the optic 207 will be in line with the Shannon criterion. The focal length of the optic 207 is for example a few hundreds of millimeters, typically 300 mm. Glass plates 209, 210 are if necessary provided on each of the arms to compensate for the dispersion.

Time-Dependent Interferometric Images.

For the time-dependent interferometric images, e.g., images obtained by Dynamic Cell Full Field Optical Coherence Tomography (DC-FFOCT), also known at Dynamic Cell Imaging (DCI), described herein, images are acquired as follows. Since the light source 201 has a low coherence length, interferences between the light reflected by the reflection surface 205 (reference wave) and that backscattered by the sample 206 occur only when the optical paths in the two arms are equal, to within the coherence length. Thus, interferences occur between the reference wave and the light backscattered by each voxel of a slice situated in a plane at right angles to the optical axis of the object arm, at a given depth of the sample, called a coherence slice, a voxel being an elementary volume defined in the coherence slice. The light backscattered by each voxel is representative of the amplitude of the coherent sum of the waves backscattered by all of the diffusing elementary structures present in this voxel. High numerical aperture microscope objectives may be used as these images do not rely upon a large depth of field. High transverse resolutions in the 0.5 to 1.5 micron range may be achieved.

The interferometric signals resulting from the optical interferences between the reference waves and the waves backscattered by the different voxels are acquired in parallel at an instant t by the acquisition device 208. The result thereof is an interferometric image S corresponding to the state of interference at a given instant t of the coherence slice. An interferometric image element or image pixel situated at a given position (x,y), defined in relation to a two-dimensional coordinate system associated with the acquisition device 208, exhibits a value S(x,y,t) which corresponds to the intensity of the interferometric signal, acquired at the instant t at the position (x,y), resulting from the interference between the wave backscattered by the voxel of corresponding position in the sample and the reference wave reflected by an elementary surface of the reflection surface 205 of the reference arm of corresponding position.

The images may further display intra-cellular metabolism of the imaged cells, by analyzing and displaying the time series for each image pixel along a few seconds (e.g., for a period of time ranging from about 1 second to about 5 seconds and at a rate of acquisition of about 100 frames per sec (fps) to about 500 fps. In some variations, the times series of images may be about 3 seconds at 300 fps.

The time-dependent interferometric image, e.g., DCI image, is computed from the time series interferograms and displays temporal variations of intensity between the N two-dimensional interferometric signals of the current slice of the sample. Each pixel IB(x,y) of the DCI image, situated at a given position (x,y), represents the value computed for this given position for a selected parameter.

In some variations, this parameter is a parameter representative of the temporal dispersion of the intensities of the N two-dimensional interferometric signals considered. Such a parameter is for example the standard deviation of the statistical distribution of the intensities. In this way, a global measurement is performed that is representative of the temporal dispersion of the light intensities backscattered at a given point of the biological tissue. A representation in image form of the values obtained for this parameter makes it possible to reveal and view the tissue regions where movements occur.

According to one or more embodiments of the imaging system, a pixel of the image exhibits at least one component, defined in relation to a colorimetric representation space, whose value is a function of the value of the chosen parameter.

For example, a pixel of the image IB which is situated at a given position (x,y) and/or at least one component of this pixel, defined in relation to a colorimetric representation space, exhibits a value which is a function of the value computed for the parameter concerned for the corresponding position (x,y) from the intensities SNi (x,y), for i=1 to N, of the N interferometric signals acquired. For example, when the colorimetric representation space used for the image IB is a representation on gray levels, the value of the pixel IB(x,y) can be equal to or a function of the value VN(x,y) to within a scaling factor so as, for example, to obtain a gray level coded on a given number of bits. For example, in the case of an image in gray levels, the zones of the sample which are animated by a significant movement and for which the value of this parameter is therefore high, emerge in such images with a high gray level. On the other hand, the parts for which no movement is detected and exhibiting a zero parameter value, will exhibit a very low gray level. In another variation, when the colorimetric representation space used for the image IB is a representation according to the RGB (Red, Green, Blue) colorimetric representation space, at least one of the components R, G or B of the pixel IB(x,y) of position (x,y) in the image IB will be equal to or a function of VN(x,y) to within a scaling factor so as, for example, to obtain a colorimetric component coded on a given number of bits. For an image analyzed for movement, in the RGB colorimetric representation space, zones of the sample which are animated by significant movement and for which the value of this parameter is therefore high, emerge in such images with a red colorimetric representation; zones with low amounts of movement are represented as blue colorimetric representation; and zones with intermediate amounts of movement are represented as green, providing an easily understandable metabolic index (MI).

Further details of image processing for the time-dependent interferometric (DCI) image is found in International Patent Application No. PCT/EP2016/057827, Boccara et al., entitled "Method and System for Full-Field Interference Microscopy Imaging", filed on Apr. 8, 2016, and published as International Application Publication WO2016162521, the entire disclosure of which is hereby incorporated by reference in its entirety.

Spatially-Dependent Interferometric Images.

For the spatially-dependent interferometric images, e.g., an image obtained using Full Field-Optical Coherence Tomography (FF-OCT), images are obtained varying the length of the object arm and the length of the reference arm, e.g., the object arm and reference arm lengths are different, using an imaging system such as system 200 described above. In some variations, a series of images may be acquired where the length of the object arm is varied, while the length of the reference arm is not changed (in all instances, the reference arm length is different from any object arm length used). The images may be processed as described in International Patent Application No. PCT/FR01/03589, Boccara et al., entitled "Method and Device for High-Speed Interferential Microscopic Imaging Of An Object", filed Nov. 15, 2001, and published as WO0240937, the entire disclosure of which is hereby incorporated by reference in its entirety.

EXAMPLES

General: A commercial FFOCT/DCI system (LLTech, Paris, France) having an isotropic resolution of 1 micron is used in all imaging.

Example 1. Diagnosis Using Deep Learning
Classification of Image Parameters Extracted with
Deep Learning Tissue samples from human breast tissue from patients are imaged, from at least 85% of total number of patients having breast cancer, and at least 5% of total patients not having breast cancer. The total number of FOV are analyzed, including one DCI image and one FF-OCT image, which are each initially processed separately. Each pair of images are subjected to the deep learning method described herein and a number of parameters are analyzed for, including any of increases in the local cell density, a range in number of cells per unit volume/area, the number of mitotic cells (e.g., having modified area and geometry), cell motility, increase in backscattered signal in cancerous cells, possibly due to an increased trafficking to support faster growth of unregulated cancerous cells, modification to extracellular matrix, and/or collagen fibers (e.g., evidence of more disorganized environments compared to healthy tissue). It is expected that the combined data from the DCI image and the FF-OCT image will produce a diagnostic accuracy of greater than 95%, with sensitivity and specificity of better than 95%.

Example 2. Diagnosis Using Deep Learning Classification of Images

Imaging and analysis was performed similarly to Experiment 1, using the multi-layer algorithm analysis as described herein. The Confusion Table for a total of 153 samples is shown in Table 3, and shows an overall accuracy of about 92%, with Sensitivity of 91.%% and Specificity of 91.8%, an improvement over the methods of Examples 3 and 4.

TABLE 3

Confusion Table for Deep Learning Analysis.

|  | Predicted Yes | Predicted No |
| --- | --- | --- |
| Actual Yes | 140 True Positive | 13 False Negative |
| Actual No | 6 False Positive | 67 True Negative |

Experiment 3. Diagnosis Using Machine Learning Classification of Features Obtained with Machine-Learning-Aided Segmentation Tissue samples from human breast tissue from 29 patients were imaged (23 patients with breast cancer, 6 without), box 710 of FIG. 7. Within each tumor sample a number (from 7 to 23) of fields of view (FOV) were analyzed, yielding a total of 298 FOV for which one DCI image and one FF-OCT image were each initially analyzed separately.

Segmentation, as shown in box 720 of FIG. 7 was performed as follows: The first step of the automatic analysis was to perform cell segmentation in the images, box 720. To do so ilastik, a free, relatively intuitive, a machine-learning tool segmentation software was used. ilastik is based on random forest classifiers. The labels were manually drawn on the DCI images in a user interface, e.g., a manual thresholded approach. Each pixel neighborhood was characterized by a set of generic nonlinear spatial transformations applied to each channel, e.g., R, G, or B, of the DCI image. Image transformations that empirically gave the best contrast were used, and the learning process was performed for about 20-30 minutes.

A similar processing and segmentation processing was run on FF-OCT images (only gray scale images) to extract fibers. The classes used was fibers, between fibers, and cells.

Based on the previous segmentation, general features can be extracted, at box 730, from individual ROIs as metrics to classify a sample (one field of view) as normal or pathological. Features used for DCI and FF-OCT are potential good indicators for cancer, even though some of them may not be relied upon in a final analysis. Since cancer is a disease arising from loss of regulatory control of cell division and duplication cycle, it leads to uncontrolled growth that increases the local cell density, the number of cells, the number of mitotic cells (with modified area and geometry), cell motility, increase in backscattered signal in cancerous cells, possibly due to an increased trafficking (increase the density of scatter in a voxel for example), modification of local environment including the extracellular matrix, and collagen fibers, often showing more disorganized environments compared to healthy tissue. Therefore all of these features were useful for feature extraction.

In order to increase performances, machine-learning classifiers in multidimensional space with Matlab® toolbox Classification learner, was used, as in box 740, to compare between many algorithms. As features, combinations of FF-OCT and DCI features were used, and used both mean and STD of values for each image when several values were obtained (e.g. for cell diameter), leading to a final number of 42 features. Table 1 summarizes the obtained scores using different strategies. Linear SVM(Support Vector Machine) with the external phenotype (given by histology on each tissue) provided diagnoses, at box 750, with 90% sensitivity and 86% specificity on individual images, but 100% sensitivity and specificity when considering the tissue and selecting tissues with a proportion of cancerous FOV above 75%.

Using this first manual thresholded analysis method, 100% sensitivity (21 true positive for 0 false positive) and 75% specificity (2 false negative and 6 true negative) in diagnosis was obtained.

TABLE 1

Algorithm comparison.

| Method | Sensitivity | Specificity |
| --- | --- | --- |
| Linear SVM with external phenotype - All Images | 90% | 86% |
| Linear SVM with external phenotype - Tissue Average | 100% | 100% |
| Linear SVM with manual phenotype - All Images | 80% | 89% |
| Linear SVM with manual phenotype - Tissue Average | 90% | 100% |
| Linear SVM with selected features - All Images | 93% | 75% |
| Linear SVM with selected features - Tissue Average | 100% | 100% |
| Linear SVM performed on average features per tissue | 95% | 100% |

Example 4. Diagnosis Using Machine Learning Classification of Features Obtained with Automatic Machine-Learning-Aided Segmentation Imaging and analysis was performed similarly as in Example 3, but an initial manual thresholding was not used. Supplementary parameters after fiber and cell segmentation included FF-OCT/DCI signal intensity, DCI MI color (e.g., speed of movement captured in images) amongst others. The confusion matrix obtained for a total of 524 FOV is shown in Table 2.

TABLE 2

Confusion Table for automatic Machine Learning.

|  | Predicted Yes | Predicted No |
| --- | --- | --- |
| Actual Yes | 385 True Positive | 28 False Negative |
| Actual No | 45 False Positive | 66 True Negative |

As shown in Table 2, combining all these parameters into the analysis yielded an overall accuracy of 86.1%. Further improvement to 100% accuracy was found by averaging over several regions of an individual biopsy, similar to how a standard histopathology process would average.

Example 5. ROSE Biopsy Experiment Using Time-Dependent Imaging and Optionally, Spatially-Dependent Imaging Real Time During Biopsy Procedure A patient is prepared within a biopsy procedural theater for excision of a biopsy sample. Imaging by ultrasound is used to guide a steerable biopsy needle to the suspected site of malignant cells. A first sample of cells is removed from the suspect region, and the cells are immediately imaged using DCI, and optionally, FF-OCT. The images are processed as described herein, and a metabolic index (MI) assigned. Determining that insufficient numbers of cells having medium to high MI are present, a second excision is made to add to the numbers of cells for analysis for that patient. After determining that the second excision sample provides enough and clinically relevant cells, by DCI, with optional FF-OCT imaging and processing, the patient's biopsy site is closed, and the cell sample transferred to Pathology/Cytopathology for preparation of permanent slides.

Example 6. Screening of Biological Agent for Treatment of Infected Cells

Colonies of *Pseudomonas aeruginosa* Gram negative bacteria is imaged by time-dependent interferometry (DCI) at time=0, within a cell vessel permitting perfusion, nutrient introduction and waste removal. A library of engineered phages having putative specificity for *P. aeruginosa* bacteria is investigated for efficacy. Each individual engineered phage population is introduced to a separate bacterial colony, and DCI imaging is performed at 1 hour intervals post administration, until 24 hours post administration. The images are processed as described above, and images having metabolic index (MI) coding are produced. The kinetics of phage killing is observed and the phage population having the best kinetics for bacterial cell killing is identified.

Example 7. Screening of Biological Agent for Treatment of Infected Cells

Mixed populations of mammalian cells such as murine epithelial cells infected by *Pseudomonas aeruginosa* Gram negative bacteria is imaged by time-dependent interferometry (DCI) at time=0, within a cell vessel permitting perfusion, nutrient introduction and waste removal. A library of engineered phages having putative specificity for *P. aeruginosa* bacteria is investigated for efficacy. Each individual engineered phage population is introduced to a separate mammalian cell/bacteria population, and DCI imaging is performed at 1 hour intervals post administration, until 24 hours post administration. The images are processed as described above, and images having metabolic index (MI) coding are produced. The effect of phage killing on the metabolism of the mammalian cells is observed as well as the kinetics of phage killing, to determine whether the lytic effects of phage killing is deleterious to the mammalian cells. The phage population having the best kinetics for bacterial cell killing and the least deleterious effect on mammalian cells is identified.

Example 8. Screening of Molecules for Treatment of Diseased Cells

A spheroid, e.g., a three dimensional cultured cell composition, containing a population of healthy human breast cells as well as cancerous breast cells, is imaged by time-dependent interferometry (DCI) at time=0, within a cell vessel permitting perfusion, nutrient introduction and waste removal. A tyrosine kinase inhibitor is administered to the spheroid at a preselected concentration and DCI imaging is performed at 1 hour intervals post administration, until 72 hours post administration. The spheroid may also be imaged by spatially-dependent interferometry (FF-OCT) at each time point. The images are processed as described above, and images having metabolic index (MI) coding are produced. The series of images are analyzed to determine whether the tyrosine kinase inhibitor is effective in killing cancerous cells. The analysis also includes determination whether the healthy cells in the spheroid are adversely affected by the administration of the tyrosine kinase, e.g., potentially exhibiting off-target effects.

Figure 8:
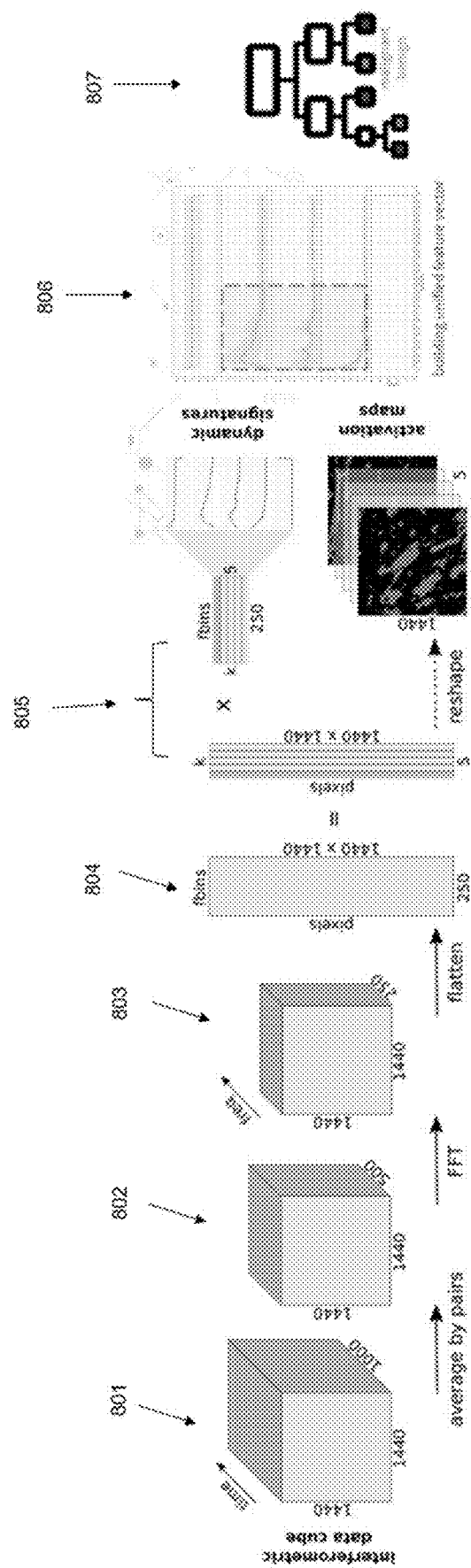
FIG. 8 is a workflow for using a Non-Negative Matrix Factorization (NMF) algorithm with DCI images of breast tissue.
Figure 9A:
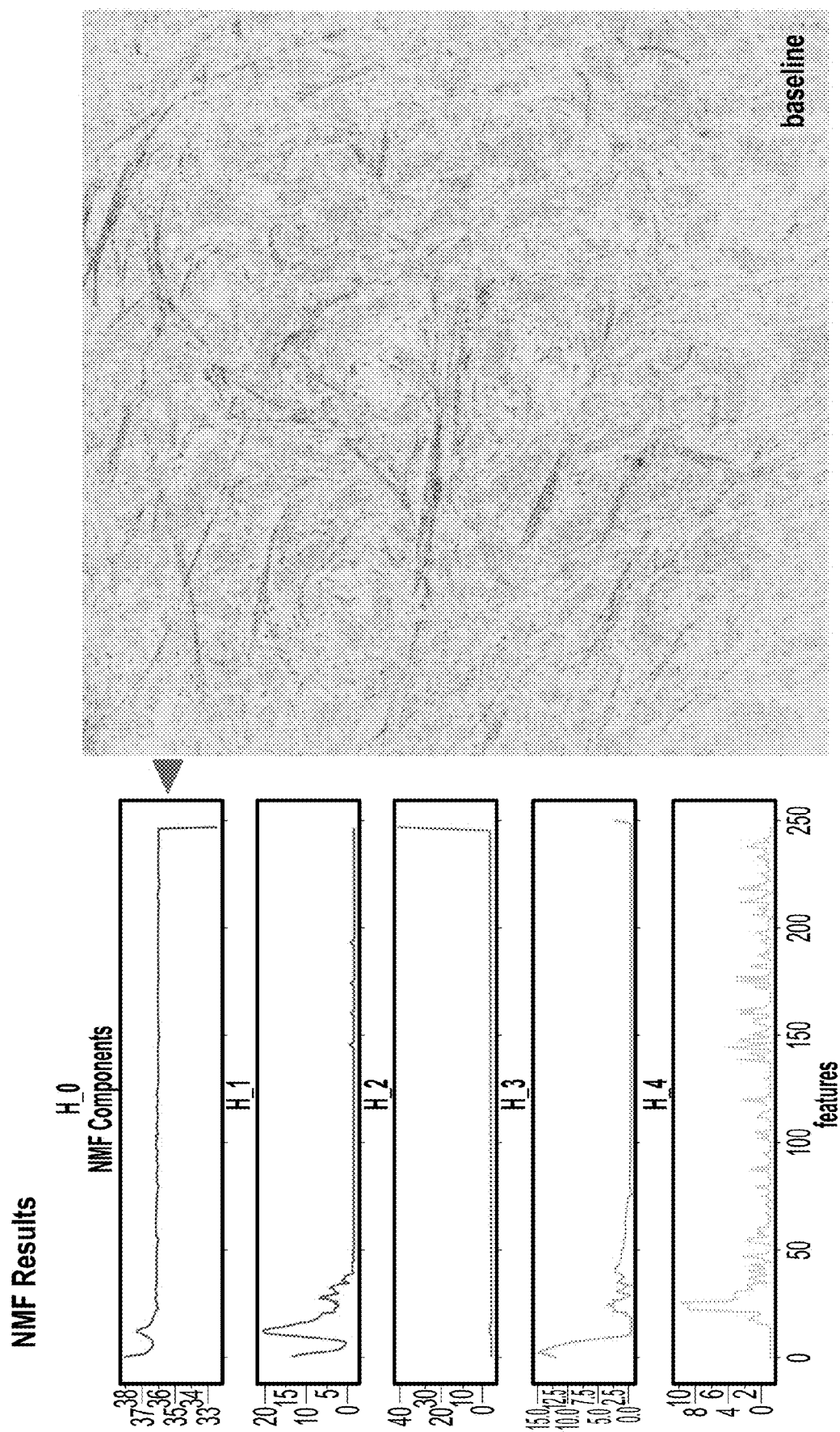
FIGS. 9A-9E show the results of the NMF analysis for baseline signal, fibers, noise, cells, and motion artifact.
Figure 9B:
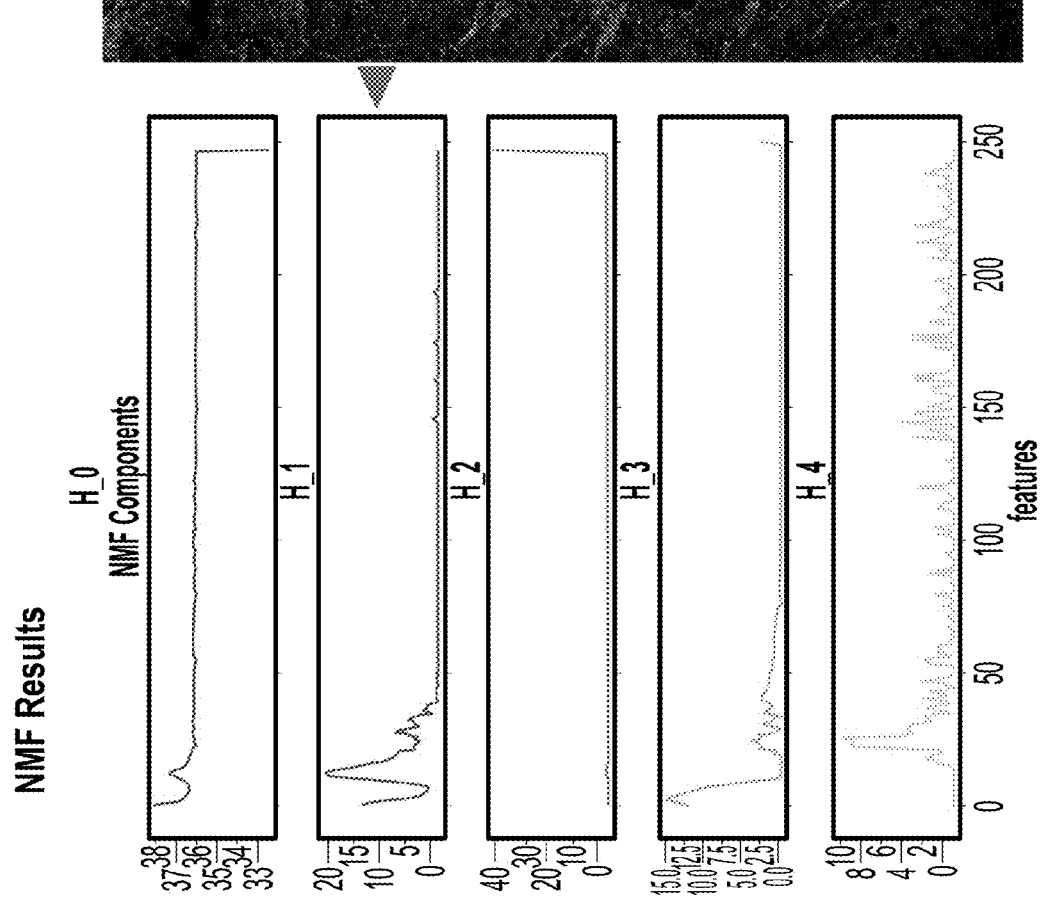
Figure 9C:
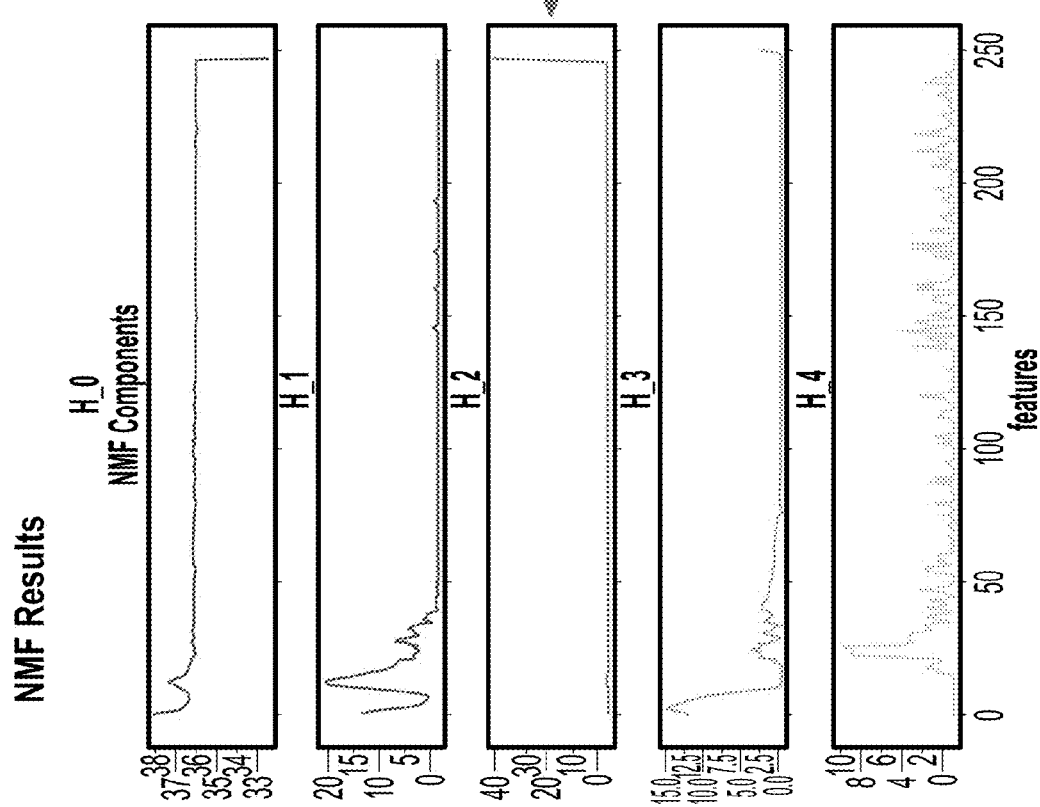
Figure 9D:
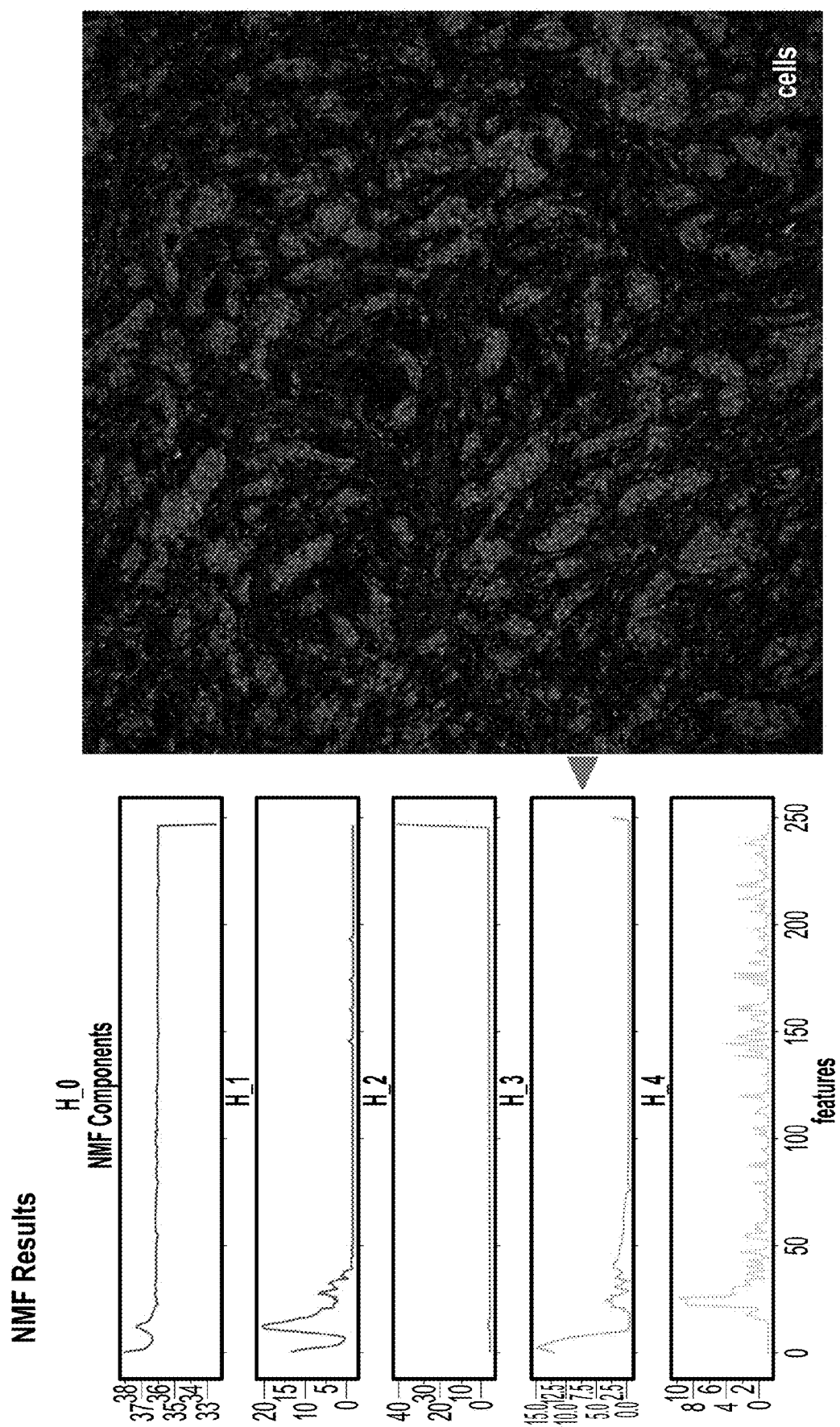
Figure 9E:
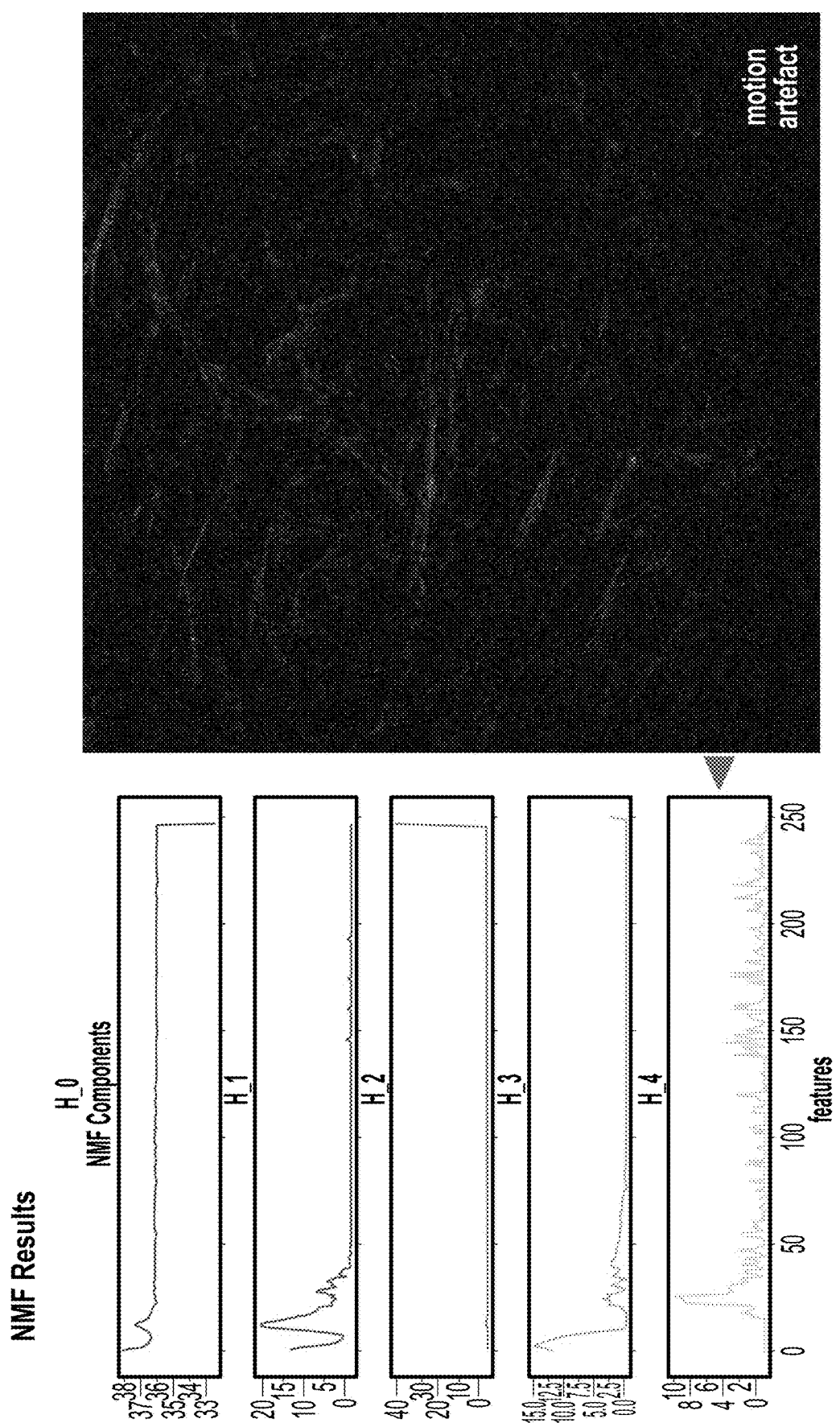

Example 9. Diagnosis Using Machine Learning Classification of Features Extracted Using Non-Negative Matrix Factorization Technique FIG. 8 illustrates a workflow for using a Non-Negative Matrix Factorization (NMF) algorithm with DCI acquisitions of breast tissue. In the illustrated example, referring to step 801, one DCI acquisition of e.g., 1000 images acquired at 150 Hz can be obtained for each FOV (resulting a time stack of interferometric frames equivalent to a data cube of 1440×1440×1000 pixels per FOV).

Next, in order to extract the pertinent metabolic information and remove the incoherent part(s) of the signal, the raw interferometric (time) domain can be transformed to the frequency domain. This can include normalizing the frames to constant energy to remove frame-to-frame inconsistences introduced by the acquisition. At step 802 of FIG. 8, the method can further include averaging the frames by groups of 2 to attenuate noise (resulting in 500 frames pseudo-acquired at 75 Hz. At step 803, the method can include passing to frequency domain with pixel-wise FFT (resulting in 250 frequency maps with a step of 0.15 Hz). Next, the method can include normalizing FFT by its norm $L_1$, and passing to logarithmic scale to compensate the skewness of the amplitude towards low frequencies. This results in a frequency stack holding both spatial and dynamical information. At step 804, the method can include flattening the frequency datacube into a 2D table of 250 rows (frequency bins) and 2073600 columns (1440×1440 pixels). As a result, the spectrum of each pixel is treated as an individual data point, disregarding the spatial configuration.

Next, at step 805 of FIG. 8, a Non-Negative Matrix Factorization (NMF) algorithm can be applied individually on the flattened frequency cube of each DCI FOV. The purpose of NMF is to factorize the data matrix X of size 2073600×250, into two low-rank positive matrices, i.e., X≈WH, where H is of size k×250 and W is of size 2073600×k. k is the number of chosen components to split into. Finding the two composing matrices is achieved by minimizing the error (e.g., squared Frobenius norm—sum of squares) between the original data matrix and the result of the factorization:

$$\min_{W \geq 0, H \geq 0} \|X - WH\|_F^2.$$

To solve this optimization problem the algorithm of multiplicative update is used; it updates alternatively and iteratively for W and H in the direction of the gradient until convergence. The rank of factorization k is empirically chosen, it can be set using some prior knowledge about the data together with trial and error experiments. For example, k can be chosen equal to 5. After NMF factorization, matrix H reveals frequency signatures and here revealed components correspond to baseline signal, fibers, noise, cells, and motion artifact. W matrix reveals the corresponding spatial activations of the frequency signatures. FIGS. 9A-9E show the results for each of the 5 components, respectively.

At next step 806 of FIG. 8, to prepare for classification, a unified feature vector is constructed for each FOV. To do this, the H components are ordered by their energy (area under curve) and the ones with the minimum and maximum energy are removed, since they correspond to the noise and baseline component, respectively. Then the 3 remaining components are concatenated to form a single feature vector that will characterize each FOV. Ordering the components by their energy also ensures some consistency of the feature vector between FOVs.

To establish a diagnosis between cancerous and normal tissue of the 382 FOVs (from 47 samples), a trained classifiers can be applied to the unified feature vector extracted form NMF (step 807 of FIG. 8). The classifier can be, for example, a tree-based classifier such as AdaBoost, XGBoost, RandomForest, ExtraTrees, GradientBoosting, DecisionTree, or the like. Using this method of classification after feature extraction with NMF, 78% sensitivity and 64% specificity in diagnosis was obtained.

Figure 10:
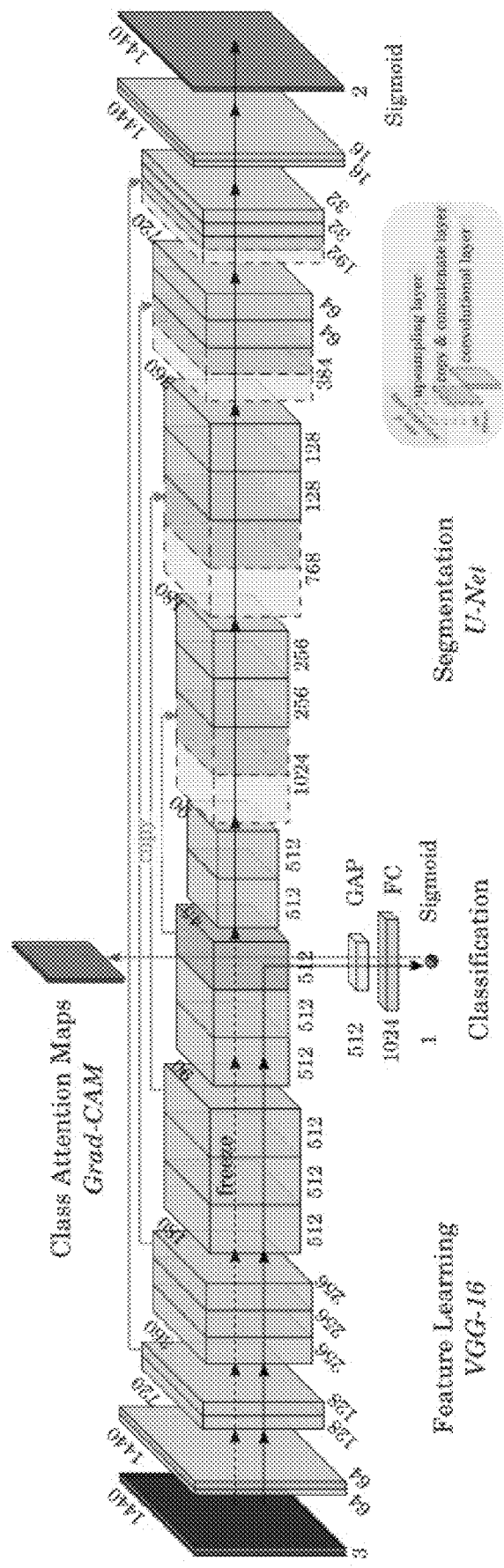
FIG. 10 is a workflow that streamlines classification and segmentation to obtain a high confidence classification jointly with a course segmentation of DCI breast specimens.

Example 10. Analysis with Deep Learning Classification, Feature Learning Via Classification and Segmentation As with example 9, the data set includes individual FOVs acquired from different locations for each sample, each FOV having 1440×1440 pixels. Each FOV can be input into a trained convolutional network for classification and detection. In this example, a pretrained VGG-16 neural network was used, as shown in FIG. 10. The VGG-16 neural network takes each FOV as an input which is passed through a stack of convolutional feature extraction layers.

A Global Average Pooling Layer (GAP) is added after the convolutional feature extraction layers which produces a feature vector size of 512 representing the average activation of each filter of the last convolutional layer of VGG-16. After pooling, the classifier is kept to a minimum of complexity with only one hidden layer of size 1024, followed by the binary output neuron with sigmoid activation.

Figure 11:
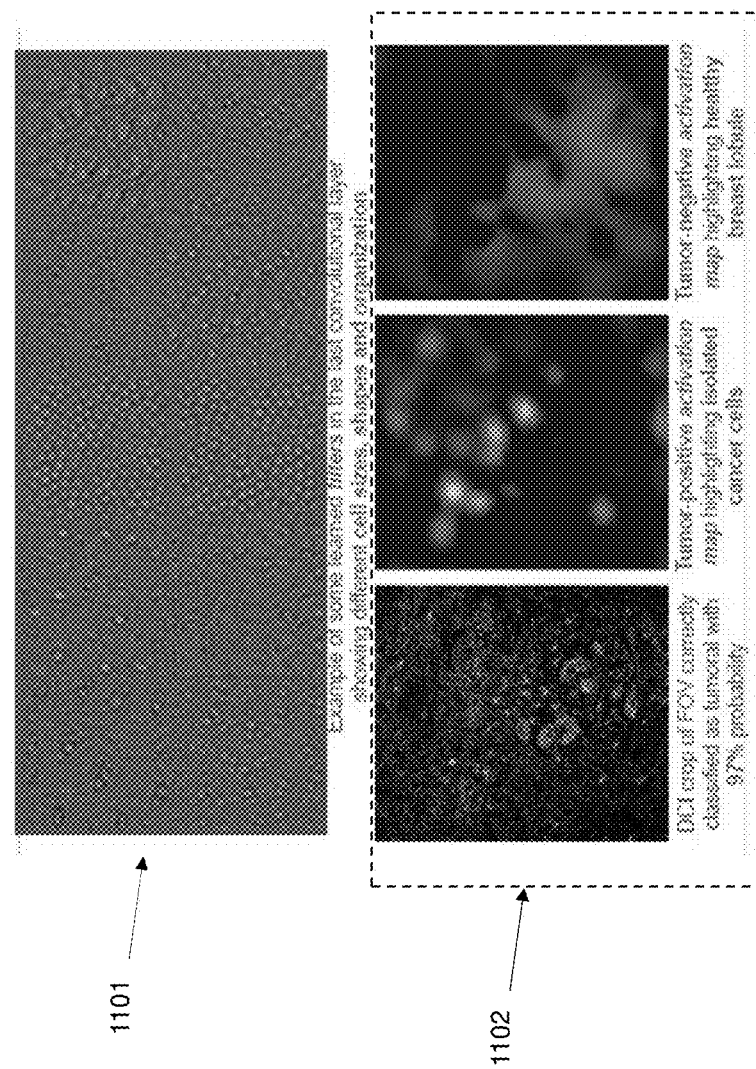
FIG. 11 illustrates some examples of filters of the deepest convolutional layer of one approach, and examples of inputs using a GradCAM method.

In a quest for interpretability and confidence in the trained model, two approaches can be followed. To verify that the learning is not limited to the classifier but has been extended to the feature extractor, synthetic inputs can be obtained through gradient ascent by maximizing the activation of each convolutional filter iteratively, and we obtain the textures learned from the data. See 1101 in FIG. 11 for an example of some filters of the deepest convolutional layer.

The second approach consists in displaying the class activation maps of several inputs using the GradCAM method, which reveals the "important" areas in an input indicating towards a certain class. This results in a coarse localization of the class presence in the input which can serve numerous purposes, an important one is verifying that the model is not biased (e.g. higher importance to context, rather than the actual object of interest or, on the other hand, a very focused attention on a small part of the object). See 1102 in FIG. 11 for an example of the positive Grad-CAM (localizing cancer cells) and the negative GradCAM highlighting a normal lobule.

The attention maps can be transformed into a segmentation mask which can serve as a ground truth for training the U-net architecture in FIG. 10, built by merging the network already trained on the classification task and adding a decoder branch.

In this example, classification and segmentation are stream-lined together to obtain a high confidence classification jointly with a course segmentation of DCI breast specimens. This approach allows a pathologist to give their feed-back and corrections with little throughput, leading to improved expert annotations.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath"

other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of determining the status of a plurality of cells, comprising:
   obtaining a time-dependent interferometric image and a spatially-dependent interferometric image of a plurality of cells suspected to comprise a cancerous cell;
   submitting the time-dependent interferometric image and the spatially-dependent interferometric image to a multi-layered algorithm analysis, thereby combining data associated at each pixel of the respective image of the plurality of cells; and
   automatically assigning a status to at least one cell of the plurality of cells, wherein the status is selected from a normal cell status or a cancerous cell status.

2. The method of claim 1, further comprising training the multi-layered algorithm analysis by analyzing a portion of data from the time-dependent interferometric image and/or a portion of data from the spatially-dependent interferometric image.

3. The method of claim 1, wherein the time-dependent interferometric image and a spatially-dependent interferometric image are spatially registered.

4. The method of claim 1, further comprising submitting an image of the plurality of cells, wherein the plurality of cells further comprise a detectable label, to the multi-layered algorithm analysis.

5. The method of claim 1, wherein the method further comprises:
   differentiating structural features of the plurality of cells; and
   reducing interference in the time-dependent interferometric image of the plurality of cells.

6. The method of claim 1, wherein the multi-layer algorithm analysis comprises a pre-trained convolutional neural network.

7. The method of claim 1, wherein the method further comprises automatically assigning a status to a sub-set of the plurality of cells, whereby a region in which the sub-set of the plurality of cells are disposed is annotated as normal or cancerous.

8. The method of claim 7, wherein a sub-set of the structural features from the spatially-dependent interferometric images are submitted to artificial intelligence such as a deep learning algorithm to thereby assign the status of the region in which the sub-set of the plurality of cells is disposed.

9. A method of performing a biopsy on a subject in need thereof, comprising:
   imaging a region of tissue to identify a region of interest;
   inserting a biopsy needle into the region of interest;
   excising a first tissue sample from the region of interest;
   obtaining a set of time-dependent interferometric images and a spatially-dependent interferometric image of the first tissue sample; and
   determining a number of cells of interest present within the first tissue sample.

10. The method of claim 9, wherein imaging the region of tissue, inserting the biopsy needle, excising the first tissue sample, obtaining the set of time-dependent interferometric images and the spatially-dependent interferometric image, and determining the number of cells of interest present are performed within a biopsy procedural theater.

11. The method of claim 9, wherein obtaining the set of time-dependent interferometric images and spatially-dependent image further comprises processing the images to obtain images of sub-cellular metabolic activity of a plurality of cells within the first tissue sample.

12. The method of claim 11, wherein the method further comprises assigning a status to one or more cells of the plurality of cells, wherein the one or more cells having the assigned status is a cell of interest.

13. The method of claim 12, wherein the assigned status is a diseased cell status.

14. The method of claim 12, wherein the diseased cell status is a cancerous cell status.

15. The method of claim 12, wherein determining a number of cells of interest comprises submitting the images of sub-cellular metabolic activity to processing by a multi-layer algorithm, thereby assigning the status to the one or more cells.

16. The method of claim 15, wherein assigning the status to the one or more cells comprises comparing a level of metabolic activity observed in the one or more cells to a preselected threshold.

17. The method of claim 9, wherein the method further comprises obtaining a second tissue sample from the region of interest, when the number of cells of interest in the first tissue sample is insufficient for analysis.

18. The method of claim 9, wherein imaging the region of tissue comprises contrast optical imaging, label-free optical imaging, radiotopic imaging, ultrasound imaging or magnetic imaging.

19. The method of claim 9, wherein inserting a biopsy needle comprises guided insertion.

\* \* \* \* \*